United States Patent
Ma et al.

(10) Patent No.: US 9,019,262 B2
(45) Date of Patent: Apr. 28, 2015

(54) SYSTEMS AND METHODS FOR TRACKING POSITIONS BETWEEN IMAGING MODALITIES AND TRANSFORMING A DISPLAYED THREE-DIMENSIONAL IMAGE CORRESPONDING TO A POSITION AND ORIENTATION OF A PROBE

(75) Inventors: Kayan Ma, Toronto (CA); Gal Sela, Toronto (CA); Cameron Piron, Toronto (CA)

(73) Assignee: Hologic, Inc., Marlborough, MA (US)

(*) Notice: Subject to any disclaimer, the term of this patent is extended or adjusted under 35 U.S.C. 154(b) by 836 days.

(21) Appl. No.: 12/954,663

(22) Filed: Nov. 25, 2010

(65) Prior Publication Data

US 2011/0134113 A1 Jun. 9, 2011

Related U.S. Application Data

(60) Provisional application No. 61/264,743, filed on Nov. 27, 2009, provisional application No. 61/394,734, filed on Oct. 19, 2010.

(51) Int. Cl.
*G06T 15/00* (2011.01)
*A61B 8/00* (2006.01)
(Continued)

(52) U.S. Cl.
CPC . *A61B 8/466* (2013.01); *A61B 8/13* (2013.01); *A61B 8/4245* (2013.01); *A61B 8/4281* (2013.01); *A61B 8/4455* (2013.01);
(Continued)

(58) Field of Classification Search
None
See application file for complete search history.

(56) References Cited

U.S. PATENT DOCUMENTS

| 3,115,140 A | 12/1963 | Volkman |
| 4,733,661 A | 3/1988 | Palestrant |

(Continued)

FOREIGN PATENT DOCUMENTS

| CN | 1640139 A | 7/2005 |
| CN | 101601266 A | 12/2009 |

(Continued)

OTHER PUBLICATIONS

Pagoulatos et al., Interactive 3-D Registration of Ultrasound and Magnetic Resonance Images Based on a Magnetic Position Sensor, Dec. 1999, IEEE Transaction on Information Technology in Biomedicine, vol. 3, No. 4, pp. 278-288.*

(Continued)

*Primary Examiner* — Aaron M Richer
*Assistant Examiner* — Anh-Tuan V Nguyen
(74) *Attorney, Agent, or Firm* — Vista IP Law Group LLP

(57) ABSTRACT

Systems and methods are provided for transforming a displayed three-dimensional image corresponding to a position and orientation of a field of view of an imaging probe. A three dimensional image of a tissue in a first co-ordinate space can be displayed. A field of view of an imaging probe in a second co-ordinate space can be configured, where the imaging probe has a plurality of transmitters removably connected to it, the transmitters operable to determine the position and orientation of the field of view relative to the positions of the transmitters in the second co-ordinate space. The first and second co-ordinate spaces can be co-registered, and the position and orientation of the field of view in the second co-ordinate space can be transformed to the first co-ordinate space. The three-dimensional image can be displayed to correspond to the transformed position and orientation of the field of view.

16 Claims, 18 Drawing Sheets

(51) Int. Cl.
*A61B 8/08* (2006.01)
*A61B 8/13* (2006.01)

(52) U.S. Cl.
CPC ............... *A61B 8/463* (2013.01); *A61B 8/465* (2013.01); *A61B 8/5238* (2013.01)

(56) References Cited

U.S. PATENT DOCUMENTS

| | | | |
|---|---|---|---|
| 4,825,162 A | 4/1989 | Roemer et al. | |
| 4,930,525 A | 6/1990 | Palestrant | |
| 5,014,968 A | 5/1991 | Lammers et al. | |
| 5,047,036 A | 9/1991 | Koutrouvelis | |
| 5,196,019 A | 3/1993 | Davis et al. | |
| 5,297,551 A | 3/1994 | Margosian et al. | |
| 5,308,352 A | 5/1994 | Koutrouvelis | |
| 5,575,798 A | 11/1996 | Koutrouvelis | |
| 5,594,337 A | 1/1997 | Boskamp | |
| 5,682,890 A | 11/1997 | Kormos et al. | |
| 5,817,023 A * | 10/1998 | William Daft | 600/447 |
| 6,159,221 A | 12/2000 | Chakeres | |
| 6,163,616 A | 12/2000 | Feldman | |
| 6,281,681 B1 | 8/2001 | Cline et al. | |
| 6,324,243 B1 | 11/2001 | Edic et al. | |
| 6,334,067 B1 | 12/2001 | Brabrand | |
| 6,421,454 B1 | 7/2002 | Burke et al. | |
| 6,421,553 B1 | 7/2002 | Costa et al. | |
| 6,591,128 B1 | 7/2003 | Wu et al. | |
| 6,628,983 B1 | 9/2003 | Gagnon | |
| 6,810,595 B2 | 11/2004 | Chan | |
| 6,950,492 B2 | 9/2005 | Besson | |
| 7,020,314 B1 | 3/2006 | Suri et al. | |
| 7,024,027 B1 | 4/2006 | Suri et al. | |
| 7,155,043 B2 | 12/2006 | Daw | |
| 7,166,113 B2 | 1/2007 | Arambula et al. | |
| 7,176,683 B2 | 2/2007 | Reeder et al. | |
| 7,245,125 B2 | 7/2007 | Harer et al. | |
| 7,245,694 B2 | 7/2007 | Jing et al. | |
| 7,545,966 B2 | 6/2009 | Lewin et al. | |
| 7,583,786 B2 | 9/2009 | Jing et al. | |
| 7,711,407 B2 | 5/2010 | Hughes et al. | |
| 7,809,426 B2 | 10/2010 | Kim et al. | |
| 7,881,428 B2 | 2/2011 | Jing et al. | |
| 7,925,328 B2 | 4/2011 | Urquhart et al. | |
| 8,155,417 B2 | 4/2012 | Piron et al. | |
| 8,162,847 B2 | 4/2012 | Wale et al. | |
| 8,162,848 B2 | 4/2012 | Hibner et al. | |
| 8,162,849 B2 | 4/2012 | Deshmukh et al. | |
| 8,241,301 B2 | 8/2012 | Zhang et al. | |
| 8,292,824 B2 | 10/2012 | Okada | |
| 8,298,245 B2 | 10/2012 | Li et al. | |
| 2002/0035864 A1 * | 3/2002 | Paltieli et al. | 73/1.01 |
| 2002/0131551 A1 | 9/2002 | Johnson et al. | |
| 2002/0193815 A1 | 12/2002 | Foerster et al. | |
| 2003/0007598 A1 | 1/2003 | Wang et al. | |
| 2003/0194050 A1 | 10/2003 | Eberhard et al. | |
| 2003/0236461 A1 * | 12/2003 | Poland | 600/443 |
| 2004/0077972 A1 | 4/2004 | Tsonton et al. | |
| 2004/0220467 A1 | 11/2004 | Bonutti | |
| 2005/0033315 A1 | 2/2005 | Hankins | |
| 2005/0251028 A1 * | 11/2005 | Boese et al. | 600/425 |
| 2005/0267373 A1 | 12/2005 | Lee | |
| 2006/0020204 A1 * | 1/2006 | Serra et al. | 600/437 |
| 2006/0122630 A1 | 6/2006 | Daum et al. | |
| 2006/0182320 A1 | 8/2006 | Peszynski et al. | |
| 2006/0221942 A1 | 10/2006 | Fruth et al. | |
| 2006/0241408 A1 | 10/2006 | Yakubovsky et al. | |
| 2006/0241432 A1 * | 10/2006 | Herline et al. | 600/437 |
| 2007/0038144 A1 | 2/2007 | Hughes et al. | |
| 2007/0083117 A1 * | 4/2007 | Sakas et al. | 600/437 |
| 2007/0149878 A1 | 6/2007 | Hankins | |
| 2007/0167705 A1 | 7/2007 | Chiang et al. | |
| 2007/0167769 A1 * | 7/2007 | Ikuma et al. | 600/437 |
| 2007/0167787 A1 * | 7/2007 | Glossop et al. | 600/447 |
| 2007/0167801 A1 | 7/2007 | Webler et al. | |
| 2007/0233157 A1 | 10/2007 | Mark et al. | |
| 2007/0238954 A1 | 10/2007 | White et al. | |
| 2007/0255168 A1 | 11/2007 | Hibner et al. | |
| 2007/0255170 A1 | 11/2007 | Hibner et al. | |
| 2007/0276234 A1 * | 11/2007 | Shahidi | 600/437 |
| 2008/0009724 A1 * | 1/2008 | Lee et al. | 600/437 |
| 2008/0033454 A1 | 2/2008 | Lukoschek et al. | |
| 2008/0095421 A1 * | 4/2008 | Sun et al. | 382/131 |
| 2008/0132912 A1 | 6/2008 | Shabaz | |
| 2008/0234569 A1 * | 9/2008 | Tidhar et al. | 600/423 |
| 2008/0269604 A1 * | 10/2008 | Boctor et al. | 600/437 |
| 2009/0024030 A1 * | 1/2009 | Lachaine et al. | 600/437 |
| 2009/0124906 A1 * | 5/2009 | Caluser | 600/443 |
| 2009/0156961 A1 | 6/2009 | Tsonton et al. | |
| 2009/0222229 A1 * | 9/2009 | Kakinami | 702/97 |
| 2009/0247861 A1 * | 10/2009 | Manus et al. | 600/424 |
| 2009/0270725 A1 | 10/2009 | Leimbach et al. | |
| 2009/0275830 A1 * | 11/2009 | Falco et al. | 600/437 |
| 2009/0307915 A1 * | 12/2009 | Sutherland | 33/502 |
| 2010/0041990 A1 | 2/2010 | Schlitt et al. | |
| 2010/0179428 A1 | 7/2010 | Pedersen et al. | |
| 2010/0249595 A1 * | 9/2010 | Xu et al. | 600/443 |
| 2010/0280354 A1 | 11/2010 | Zhang et al. | |
| 2010/0324445 A1 | 12/2010 | Mollere et al. | |
| 2010/0324448 A1 | 12/2010 | Mollere | |
| 2011/0134113 A1 | 6/2011 | Ma et al. | |
| 2011/0153254 A1 * | 6/2011 | Hartov et al. | 702/103 |
| 2013/0053684 A1 | 2/2013 | Piron et al. | |

FOREIGN PATENT DOCUMENTS

| | | |
|---|---|---|
| EP | 2503934 A1 | 10/2012 |
| WO | 2006017172 A1 | 2/2006 |
| WO | 2007070285 A2 | 6/2007 |
| WO | 2011134113 A1 | 11/2011 |

OTHER PUBLICATIONS

Khamene et al., A Novel Phantom-Less Spatial and Temporal Ultrasound Calibration Method, 2005, Medical Image Computing and Computer-Assisted Intervention, pp. 65-72.*

Chen et al., A Real-Time Freehand Ultrasound Calibration System with Automatic Accuracy Feedback and Control, Jan. 2009, Ultrasound in Medicine and Biology, vol. 35, No. 1, pp. 79-93.*

Piron, Cameron A., Hybrid Imaging Guidance System for Biopsy of the Breast, Thesis Paper, University of Toronto, 2001.

General Electric—Press Release—"GE Healthcare Introduces Ultrasound Fusion; New LOGIQ E9 Merges Real-time Ultrasound with CT, MR and PET," Sep. 2, 2008, 2 pages.

International Preliminary Report of Patentability for International Application No. PCT/CA2010/001871 dated May 30, 2012, 1 page.

International Search Report and Written Opinion of the International Searching Authority for International Application No. PCT/CA2010/001871 dated Mar. 8, 2011, 9 pages.

M. Berger, "Image Fusion and Needle Guidance in Ultrasound", General Electric, Power Point Presentation, date unknown, 17 pages.

P. Mullen and C. Owen, "MR, Ultrasound Fusion: Bridging the Gap Between Clinical Benefits, Access and Equipment Utilization," SignaPULSE—a GE Healthcare MR Publication, Spring 2009, 5 pages.

International Search Report for International Application No. PCT/CA2010/000973, mailed Oct. 1, 2010, 3 pages.

Notification of Transmittal of the International Search Report and the Written Opinion of the International Searching Authority, or the Declaration for International Application No. PCT/US2013/053947, mailed Nov. 13, 2013, 10 pages.

* cited by examiner

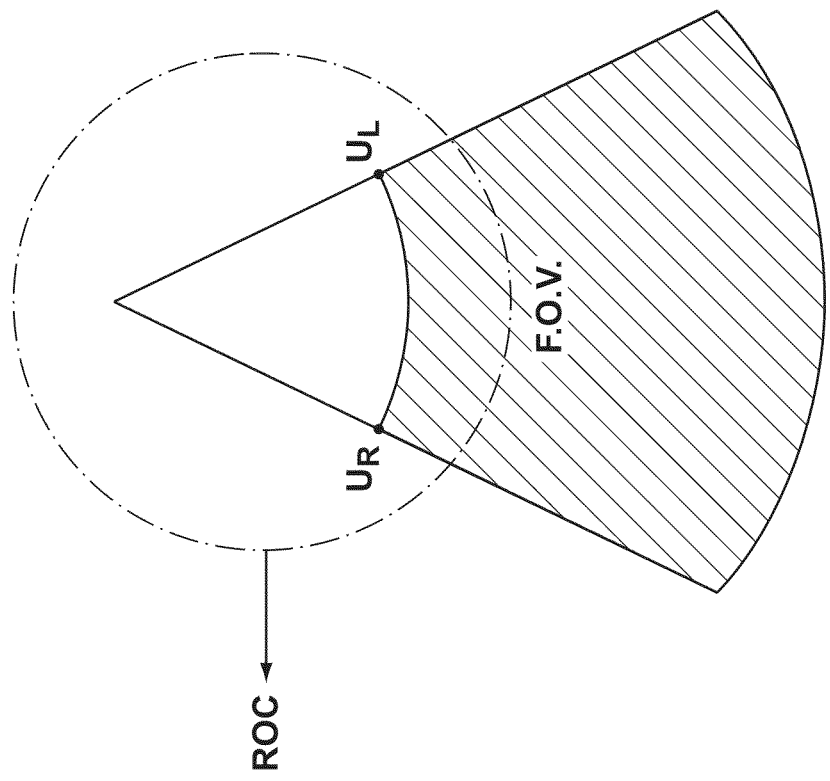
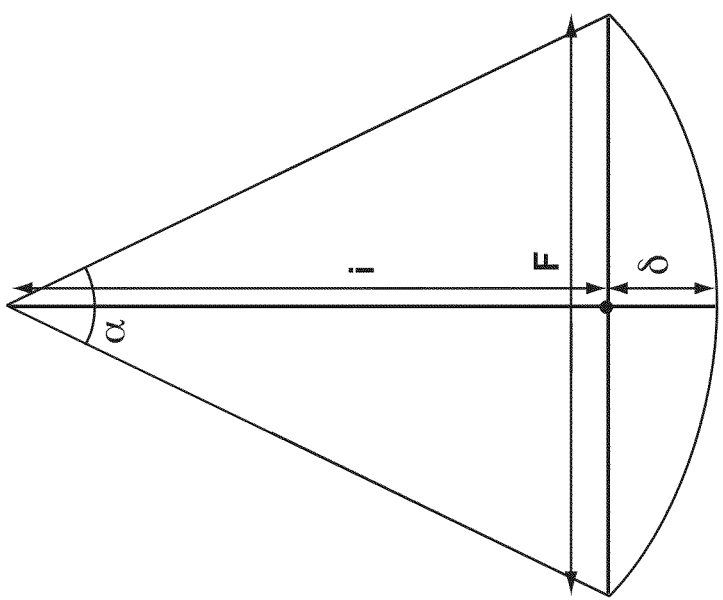
FIG. 20

SYSTEMS AND METHODS FOR TRACKING POSITIONS BETWEEN IMAGING MODALITIES AND TRANSFORMING A DISPLAYED THREE-DIMENSIONAL IMAGE CORRESPONDING TO A POSITION AND ORIENTATION OF A PROBE

RELATED APPLICATIONS

This application claims priority from U.S. Provisional Application No. 61/264,743 filed Nov. 27, 2009 and U.S. Provisional Application No. 61/394,734 filed Oct. 19, 2010, the contents of each of which are herein incorporated by reference.

FIELD OF THE INVENTION

This invention relates to the field of medical imaging and more specifically relates to dynamically transforming a displayed three dimensional medical image of a tissue.

BACKGROUND

Medical imaging devices provide non-invasive methods to visualize the internal structure of a patient. Such non-invasive visualization methods can be helpful in treating patients for various ailments. For example, the early detection of cancer in a patient can be important in treating that patient. For most cancers, when detected at an early stage, the survival probability of the patient can increase.

There are many medical imaging methods available for visualizing the internal structure of a patient, each with its own benefits and its own limitations and while the examples and embodiments described herein relate to MRI systems, MRI scanners and MRI images, any displayed three-dimensional image can be dynamically transformed using the systems and methods described herein, for example a three-dimensional CT image, three-dimensional optical coherence tomography image, or other three-dimensional medical image of a tissue of a patient such as single photon emission computed tomography or positron emission tomography. Additionally, it will be appreciated there are many medical imaging methods that use a probe having a field of view and while the examples and embodiments described herein relate to ultrasound systems having a field of view, any medical imaging method having a field of view can be used in the systems and methods described herein, including OCT (optical) sensors and PET detectors.

Magnetic resonance imaging (MRI) is one such non-invasive medical imaging technique which uses magnetic fields to image tissue of a patient. A patient is placed inside a powerful uniform magnetic field of an MRI scanner, which can align the magnetic moments of protons in the tissue (typically hydrogen protons of water molecules in the tissue) in the direction of the field, precessing about the field at their Larmor frequency. An excitation magnetic field (typically orthogonal to the main magnetic field) near the Larmor frequency is applied to alter the alignment of the protons in the tissue, typically flipping the magnetic moment of the protons in the main field. When the excitation field is turned off, the protons emit a photon that can be detected and processed to form an MRI image of the tissue.

Ultrasound imaging, another non-invasive medical imaging technique, uses sound waves, typically produced by piezoelectric transducers to image a tissue in a patient. The ultrasound probe focuses the sound waves, typically producing an arc-shaped sound wave which travels into the body and is partially reflected from the layers between different tissues in the patient. The reflected sound wave is detected by the transducer and converted into electrical signals that can be processed by the ultrasound scanner to form an ultrasound image of the tissue.

Each of MRI imaging and ultrasound imaging has certain advantages and certain drawbacks. For example, ultrasound tends to provide improved imaging of tendon structure in a patient over the images of the same tendon structure provided by an MRI. Ultrasound tends to provide superior spatial resolution over similar images obtained by an MRI machine.

MRI imaging tends to provide superior soft-tissue contrast resolution as compared to ultrasound images, typical MRI images tending to allow individual structures such as a lung, liver, kidney, bowel, and gray and white matter to be distinguished. Additionally, ultrasound provides a smaller field-of-view as compared to MRI imaging, and the resolution of ultrasound images tends to be restricted by the sound wave penetration through soft tissues and bone. For example, ultrasound imaging has difficulty penetrating bone and thus typically only sees the outer surface of bone structure and not what lies within.

An advantage of ultrasound as compared to MRI imaging is that ultrasound imaging provides real-time feedback. For example, an ultrasound technician can position the ultrasound transducer directly on a patent in a first position and view the ultrasound image in real time. Subsequently, the technician can move the ultrasound transducer to a second, perhaps more desirable position, to view the new ultrasound image, again in real time. This ability too adjust the position of the transducer, while viewing the ultrasound image in real time, provides the technician the ability adjust the ultrasound image until they are satisfied with the displayed image. Real-time imaging can be helpful during biopsy, where the ultrasound transducer can be used to view an image of the biopsy tool in real-time, for example a biopsy needle as it is inserted in the tissue.

It would be advantageous to combine the advantages of MRI imaging (or any three-dimensional medical image such as single positron emission computed tomography, computed tomography, positron emission tomography, fluoroscopy or endoscopy) and ultrasound imaging, to view an image of a tissue in a patient simultaneously using multiple imaging techniques. By tracking the movement of an ultrasound probe and dynamically adjusting a MRI image (or any three-dimensional medical image), for example, to show the slice of the tissue in the MRI image currently being imaged by the ultrasound imaging device, a user is provided with two images of the same tissue at the same time, taking advantage of the benefits of multiple imaging techniques.

SUMMARY OF THE INVENTION

In an aspect of the present invention, a method for transforming a displayed three-dimensional image corresponding to a position and orientation of a field of view of an imaging probe is described, the method comprising displaying a three dimensional image of a tissue having a first co-ordinate space; calibrating the field of view of the imaging probe in a second co-ordinate space to a plurality of transmitters removably connected to the imaging probe, the transmitters operable to determine the position and orientation of the field of view relative to the positions of the transmitters in the second co-ordinate space; co-registering the first and second co-ordinate spaces; transforming the position and orientation of the field of view in the second co-ordinate space to the first co-ordinate space; and displaying the three-dimensional image to correspond to the transformed position and orientation of the field of view.

In some embodiments, the calibrating of the field of view of the imaging probe can comprise positioning a configuration tool at configuration positions on a transducer of the imaging probe and determining a calibration matrix. In some embodiments, the calibration positions can be corners of a face of the transducer.

In some embodiments, the calibration matrix can relate a transducer co-ordinate frame in the second co-ordinate space to a transmitter co-ordinate frame in the second co-ordinate space, wherein the transducer co-ordinate frame has an origin (O) at a midpoint of the face of the transducer.

In some embodiments, the calibration matrix can be a 4×4 matrix and can be determined by: determining the origin (O) specified in co-ordinates in the transmitter co-ordinate frame; determining a first vector (X) that can be normal to a face of the transducer at the origin (O) specified in co-ordinates in the transmitter co-ordinate frame; determining a second vector (Y) that can be perpendicular to the field of view and containing the origin (O) specified in co-ordinates in the transmitter co-ordinate frame; determining a third vector (Z) that can be orthogonal to the first and second vectors and containing the origin (O) specified in co-ordinates in the transmitter co-ordinate frame; and defining the calibration matrix which can be [X Y Z O; 0 0 0 1] and can be capable of relating the transducer co-ordinate frame to the transmitter co-ordinate frame in the second co-ordinate space.

In some embodiments, the transducer can be curvilinear in shape and the method further comprises shifting the position of the origin (O) to compensate for the curvilinear shape of a the face of the transducer.

In some embodiments, the method may further comprise checking for errors in calibrating the field of view.

In some embodiments, the co-registering of the first and second co-ordinate spaces can comprise determining a 4×4 transformation matrix having a rotational component and a translational component. In some embodiments, the rotational component can be determined by: selecting an anatomical plane; determining the orientation of the selected anatomical plane in the first co-ordinate space; positioning the imaging probe in the orientation of the anatomical plane; determining the rotational component being the relative rotational differences between the orientation of the field of view of the imaging probe in the second co-ordinate space with the selected anatomical plane in the first co-ordinate space.

In some embodiments the translational component can be determined by: selecting a landmark in the three-dimensional image, the landmark having a position in the first co-ordinate space; locating the landmark in the field of view; determining the position of the landmark in the second co-ordinate space; and determining the translational component being the relative difference between the position of the landmark in the first co-ordinate space and the position of the landmark in the second co-ordinate space.

In some embodiments, determining the position of the landmark in the second co-ordinate space can comprise: determining an axial distance to the landmark, wherein the axial distance is the perpendicular distance from the landmark to a line formed between an upper right corner of the field of view and an upper left corner of the field of view; and determining a lateral distance to the landmark, wherein the lateral distance is the distance to the landmark from a midpoint of the line when the landmark is projected onto the line. In embodiments where the field of view is curvilinear in shape, the method can further comprise offsetting the axial distance to compensate for the curvilinear shape of the field of view.

In some embodiments the landmark can be an internal tissue landmark and in other embodiments the landmark can be an external landmark.

In some embodiments, the three dimensional image is an MRI image and the imaging probe is an ultrasound imaging probe.

In another aspect of the present invention a method for calibrating a field of view of an imaging probe relative to a plurality of transmitters removably connected to the imaging probe is provided, the method comprising: positioning a configuration tool at configuration positions on a transducer of the imaging probe and determining a calibration matrix, wherein the calibration matrix relates a transducer co-ordinate frame to a transmitter co-ordinate frame, wherein the transducer co-ordinate frame has an origin (O) at a center of a face of the transducer.

In some embodiments, the calibration positions can be corners of the transducer. In some embodiments, the calibration matrix can be a 4×4 matrix and can be determined by: determining the origin (O) specified in co-ordinates in the transmitter co-ordinate frame; determining a first vector (X) that can be normal to transducer at the origin (O) specified in co-ordinates in the transmitter co-ordinate frame; determining a second vector (Y) that can be perpendicular to the field of view and containing the origin (O) specified in co-ordinates in the transmitter co-ordinate frame; determining a third vector (Z) that can be orthogonal to the first and second vectors and containing the origin (O) specified in co-ordinates in the transmitter co-ordinate frame; defining the transformation matrix as [X Y Z O; 0 0 0 1] capable of relating the transducer co-ordinate frame to the transmitter co-ordinate frame.

In some embodiments, the transducer can be curvilinear in shape and the method can further comprise the step of shifting the position of the origin (O) to compensate for the curvilinear shape of the face of the transducer.

In another aspect of the present invention a method of co-registering a first co-ordinate space with a second co-ordinate space is provided, the method comprising: determining a 4×4 transformation matrix capable of transforming a co-ordinate in the first co-ordinate space to the second co-ordinate space, the transformation matrix having a rotational component and a translational component; wherein the rotational component is determined by: selecting a plane; determining the orientation of the selected plane in the first co-ordinate space; positioning a probe having a plurality of transmitters removably connected thereto, the transmitters operable to determine the position and orientation of the probe in the second co-ordinate space; determining the rotational component being the relative rotational differences between the orientation the probe in the second co-ordinate space with the selected plane in the first co-ordinate space; and the translational component is determined by: selecting a landmark in the first co-ordinate space; locating the landmark in the second co-ordinate space; determining the position of the landmark in the second co-ordinate space; and determining the translational component being the relative difference between the position of the landmark in the first co-ordinate space and the position of the landmark in the second co-ordinate space.

In a further aspect of the present invention an apparatus for transforming a displayed three-dimensional image corresponding to a position and orientation of a field of view of an imaging probe is provided, the apparatus comprising: a three dimensional image of a tissue having a first co-ordinate space; a tracking module in communication with a tracking system capable of tracking the positions of a plurality of transmitters removably connected to the imaging probe; a calibration module capable of calibrating the field of view of the imaging probe relative to the tracked positions of the plurality of transmitters in the second co-ordinate space; a transformation module capable of co-registering the first and second co-ordinate spaces; an image processing module capable of transforming the position and orientation of the field of view in the second co-ordinate space to the first co-ordinate space; and a display capable of displaying the three-dimensional image to correspond to the transformed position and orientation of the field of view.

In some embodiments, the apparatus may further comprise an error correction capable of checking for errors in calibrating the field of view.

In another aspect of the present invention, a computer-readable medium is provided, the computer readable medium having instructions thereon for causing a processor to execute the instructions, the instructions adapted to be executed to implement a method for transforming a displayed three-dimensional image corresponding to a position and orientation of a field of view of an imaging probe, the method comprising: displaying a three dimensional image of a tissue having a first co-ordinate space; calibrating the field of view of the imaging probe in a second co-ordinate space to a plurality of transmitters removably connected to the imaging probe, the transmitters operable to determine the position and orientation of the field of view relative to the positions of the transmitters in the second co-ordinate space; co-registering the first and second co-ordinate spaces; transforming the position and orientation of the field of view in the second co-ordinate space to the first co-ordinate space; and displaying the three-dimensional image to correspond to the transformed position and orientation of the field of view.

In another aspect of the present invention, a method for determining the co-ordinates of a landmark visible in a field of view of an ultrasound image in a co-ordinate space is provided, the method comprising: calibrating the field of view of the ultrasound probe with a plurality of transmitters removably connected to the imaging probe, the transmitters operable to determine the position and orientation of the field of view relative to the positions of the transmitters in the co-ordinate space; determining a calibration matrix that relates a transducer co-ordinate frame in the co-ordinate space to a transmitter co-ordinate frame in the co-ordinate space, wherein the transducer co-ordinate frame has an origin (O) at a midpoint of a face of the transducer; determining the co-ordinates of the landmark in the field of view relative to a midpoint of a line formed between the upper right corner of the field of view and an upper left corner of the field of view by: determining an axial distance to the landmark in the field of view, wherein the axial distance is the perpendicular distance from the landmark to the line; and determining a lateral distance to the landmark in the field of view, wherein the lateral distance is the distance to the landmark when the landmark is projected onto the line; and transforming the co-ordinates of the landmark in the field of view into the co-ordinate space using the calibration matrix.

In embodiments where transducer is curvilinear in shape and the method may further comprise offsetting the axial distance to compensate for the curvilinear shape of the transducer.

In another aspect of the system and methods described herein, systems and methods are provide a means of registering an ultrasound image space with a tracked co-ordinate space, in some embodiments the co-ordinate system of an optical or magnetic tracking system.

In another aspect of the systems and methods described herein, systems and methods are provided that can be used with any ultrasound transducer with a scan head that has four identifiable corners (including linear, curvilinear, array and phased array transducers).

In other aspects, systems and methods are provided that can perform platform independent co-registration between two imaging modalities, such as ultrasound and MRI, without communications between them. In some embodiments, systems and methods described herein can reformat three-dimensional image data to match real-time two-dimensional ultrasound data without direct communication with the ultrasound machine.

In a further aspect of the systems and methods described herein, systems and methods are provided that can be used with any six degree of freedom (6-DOF) positional tracking system, such as optical tracking systems, radiofrequency magnetic tracking systems, mechanical linkage tracking systems and fiber optic positioning devices.

In other aspects, systems and methods are provided that can be performed by a single operator and can be implemented with minimal additional hardware which may simply the systems and methods and may allow such systems and methods to be performed with improved efficiency.

BRIEF DESCRIPTION OF THE DRAWINGS

For a better understanding of embodiments of the system and methods described herein, and to show more clearly how they may be carried into effect, reference will be made by way of example, to the accompanying drawings in which:

FIG. 20 shows a mathematical model useful in determining the offset of a target in a field of view of a curvilinear ultrasound probe.

DETAILED DESCRIPTION

Figure 1:
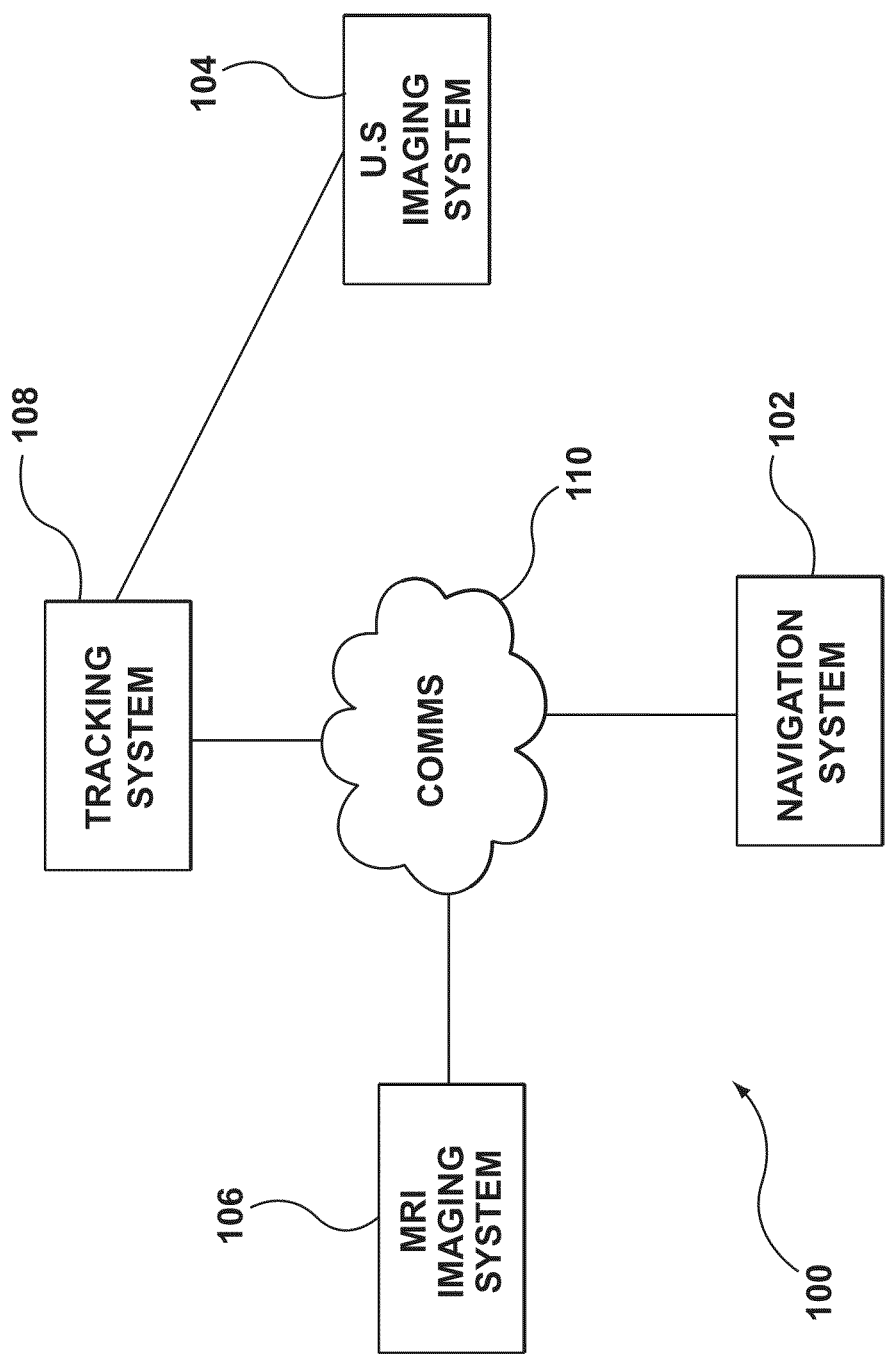
FIG. 1 shows an embodiment of a system for dynamically transforming a displayed three-dimensional image.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. In an embodiment these systems and methods are implemented in computer programs executing on programmable computers each comprising at least one processor, a data storage system (including volatile and non-volatile memory and/or storage elements), at least one input device, and at least one output device. For example and without limitation, the programmable computers may be a mainframe computer, server, personal computer, laptop, personal data assistant, or cellular telephone. Program code is applied to input data to perform the functions described herein and generate output information. The output information is applied to one or more output devices, in known fashion.

Each program can be implemented in a high level procedural or object oriented programming and/or scripting language to communicate with a computer system. However, the programs can be implemented in assembly or machine language, if desired. In any case, the language may be a compiled or interpreted language. Each such computer program can be stored on a storage media or a device (e.g. ROM or magnetic diskette) readable by a general or special purpose programmable computer, for configuring and operating the computer when the storage media or device is read by the computer to perform the procedures described herein. The embodiments may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

With reference to FIG. 1, an embodiment of system 100 is shown. System 100 has MRI imaging system 106, tracking system 108, ultrasound imaging system 104 and navigation system 102. In the embodiment shown, MRI imaging system 106, tracking system 108 and navigation system 102 are communicatively connected via communication network 110 and ultrasound imaging system 104 in a stand-alone system. However, skilled persons will understand that in some embodiments, ultrasound imaging system 104 can additionally be communicatively connected via communication network 110. Skilled persons will additionally appreciate that communication network 110 can be a local area network, wide area network, wireless network, internet, intranet, or other similar communication network.

MRI imaging system 106 obtains an MRI image of a tissue of a patient. The MRI image obtained is stored locally on MRI imaging system 106 or in some embodiments in a Picture Archiving Communications System (PACS). Typically, the image format of the MRI image is a DICOM format, however, skilled persons will understand that other image formats can be used.

Once a tissue of a patient is imaged with MRI imaging system 106, the stored image of the tissue can be reconstructed into a three-dimensional ("3D") image of the tissue and can be displayed by MRI imaging system 106, or another workstation. The MRI image, when displayed by MRI imaging system 106, can be reformatted and repositioned to view the tissue image at any plane and any slice position.

MRI imaging system 106 transmits the MRI image to navigation system 102 via communication network 110, where such MRI image can be stored and viewed. Skilled persons will understand that the MRI image of a patient can, in alternative embodiments, be stored locally on MRI imaging system 106 and accessed remotely by navigation system 102 via communications network 110, and in other embodiments can be stored on a server in communication with navigation system 102 via communications network 110. Navigation system 102 displays the MRI image obtained by MRI imaging system and once reconstructed for display on navigation system 102 the MRI image can be reformatted and repositioned to view the image at any plane and any slice position or orientation. In some embodiments navigation system 102 displays multiple frames or windows on the same screen showing alternative positions or orientations of the MRI-image slice.

Skilled persons will understand that the MRI image obtained by MRI imaging system 106 can be transmitted to navigation system 102 at any point in time and is not necessarily transmitted immediately after obtaining the MRI image, but instead can be transmitted on the request of navigation system 102. In alternative embodiments, the MRI image is transmitted to navigation system 102 by a transportable media device, such as a flash drive, CD-ROM, diskette, or other such transportable media device.

Ultrasound imaging system 104 obtains an ultrasound image of a tissue of a patient, typically using an ultrasound probe, which is used to image a portion of a tissue of a patient within the field of view of the ultrasound probe. Ultrasound imaging system 104 obtains and displays an ultrasound image of a patient's anatomy within the field of view of the ultrasound probe and typically displays the image in real-time as the patient is being imaged. In some embodiments, the ultrasound image can additionally be stored on a storage medium, such as a harddrive, CD-ROM, flash drive or diskette, for reconstruction or playback at a later time.

In some embodiments, navigation system 102 can access the ultrasound image, and in such embodiments ultrasound imaging system 104 is further connected to communication network 110 and a copy of the ultrasound image obtained by ultrasound imaging system 104 can be transmitted to navigation system 102 via communication network 110. In other embodiments, navigation system 102 can remotely access and copy the ultrasound image via communication network 100, and in alternative embodiments, a copy of the ultrasound image can be stored on a server in communication with navigation system 102 via communications network 110 and accessed remotely by navigation system 102.

Tracking system 108 is in communication with navigation system 102 via communications network 110 and tracks the physical position in which ultrasound imaging system 104 is imaging the tissue of the patient. In some embodiments, tracking system 108 can be connected directly to navigation system 102 via a direct communication link or wireless communication link. Tracking system 108 tracks the position of transmitters connected to ultrasound imaging system 104 and provides navigation system 102 with data representing their co-ordinates in a tracker co-ordinate space. In some embodiments, tracking system may be an optical tracking system comprising an optical camera and optical transmitters, however skilled persons will understand that any device or system capable of tracking the position of an object in space can be used. For example, skilled persons will understand that in some embodiments an RF tracking system can be used, comprising an RF receiver and RF transmitters.

Ultrasound imaging system 104 is configured for use with navigation system 102 by a calibration process using tracking system 108. Transmitters that are removably connected to the ultrasound probe of ultrasound imaging system 104 can transmit their position to tracking system 102 in the tracker co-ordinate space, which in turn provides this information to navigation system 102. For example, transmitters may be positioned on the probe of ultrasound imaging system 104 so that tracking system 108 can monitor the position and orientation of the ultrasound probe and provide this information to navigation system 102 in the tracker co-ordinate space. Navigation system 102 can use this tracked position to determine the position and orientation of the transducer, an ultrasound probe, relative to the tracked position of the transmitters.

In some embodiments, configuration occurs using a configuration tool, where its position and orientation can be additionally tracked by tracking system 108. During configuration the configuration tool contacts the transducer face of the ultrasound probe of ultrasound imaging system 104 and tracking system 108 transmits information representing the position and orientation of the configuration tool in the tracker co-ordinate space to navigation system 102. Navigation system 102 can determine a configuration matrix that can be used to determine the position and orientation of the field of view of the ultrasound probe in the tracker co-ordinate space, based on the tracked position of the transmitters connected to the ultrasound probe. In alternative embodiments, a database having configuration data of a plurality of brands or models of various ultrasound probes can be used to pre-load a field of view configuration into navigation system 102 during configuration.

Once ultrasound imaging system 104 is configured with navigation system 102, the tissue of a patient can be imaged with ultrasound imaging system 104. During ultrasound imaging, tracking system 108 monitors the position and orientation of the ultrasound probe of ultrasound imaging system 104 and provides this information in the tracker co-ordinate space to navigation system 102. Since ultrasound imaging system 104 has been configured for use with navigation system 102, navigation system 102 is able to determine position and orientation of the field of view of the ultrasound probe of ultrasound imaging system 104.

Navigation system 102 can be configured to co-register an ultrasound image with an MRI image. In some embodiments, navigation system 102 can be configured to transform the position and orientation of the field of view of the ultrasound probe from the tracker co-ordinate space to a position and orientation in the MRI image, for example, to DICOM co-ordinates. This can be accomplished by tracking the position and orientation of the ultrasound probe and transmitting this positional information in the tracker co-ordinate space to navigation system 102 and relating this positional information to the MRI co-ordinate system. For example, in some embodiments, a user can select an anatomical plane within the MRI image, and the user can then manipulate the position and orientation of a tracked ultrasound probe to align the field of view of the ultrasound probe with the selected anatomical plane. Once alignment is achieved, the associated tracker co-ordinate space co-ordinates of the ultrasound image can be captured. Registration of the anatomic axes (superior-inferior (SI), left-right (LR) and anterior-posterior (AP)) between the MRI image and the tracker co-ordinate space can be determined from the relative rotational differences between the tracked ultrasound field of view orientation and the selected anatomical plane.

This configuration further includes the selection of landmark within the MRI image, for example, using an interface permitting a user to select an anatomical target. In some embodiments, the landmark can be an internal tissue landmark, such as tendon, bone, veins or arteries, and in other embodiments, the landmark can be an external landmark, such as a fiducial skin marker or external landmark, such as a navel or nipple. The same landmark selected in the MRI image can be located with the ultrasound probe, and upon location, a mechanism can be provided for capturing coordinates of the representation of the target in the tracker co-ordinate space. The relative differences between the coordinates of the target in the MRI image and the co-ordinates of the target in the tracker co-ordinate space are used to determine the translational parameters required to align the two co-ordinate spaces. The plane orientation information acquired previously can be combined with the translation parameters to provide a complete 4×4 transformation matrix capable of co-registering the two co-ordinate spaces.

Navigation system 102 can then use the transformation matrix to reformat the MRI image being displayed so that the slice of tissue being displayed is in the same plane and in the same orientation as the field of view of the ultrasound probe of ultrasound imaging system 104. Matched ultrasound and MRI images may then be displayed side by side, or directly overlaid in a single image viewing frame. In some embodiments, navigation system 102 can display additional MRI images in separate frames or positions on a display screen. For example, the MRI image can be displayed with a graphical representation of the field of view of ultrasound imaging system 104 wherein the graphical representation of the field of view is shown slicing through a 3D representation of the MRI image. In other embodiments annotations can be additionally displayed, these annotations representing, for example, the position of instruments imaged by ultrasound imaging system 104, such as biopsy needles, guidance wires, imaging probes or other similar devices.

In other embodiments, the ultrasound image being displayed by ultrasound imaging system 104 can be superimposed on the slice of the MRI image being displayed by navigation system 102 so that a user can view both the MRI and ultrasound images simultaneously, overlaid on the same display. In some embodiments, navigation system 102 can enhance certain aspects of the super imposed ultrasound or MRI images to increase the quality of the resulting combined image.

Figure 2:
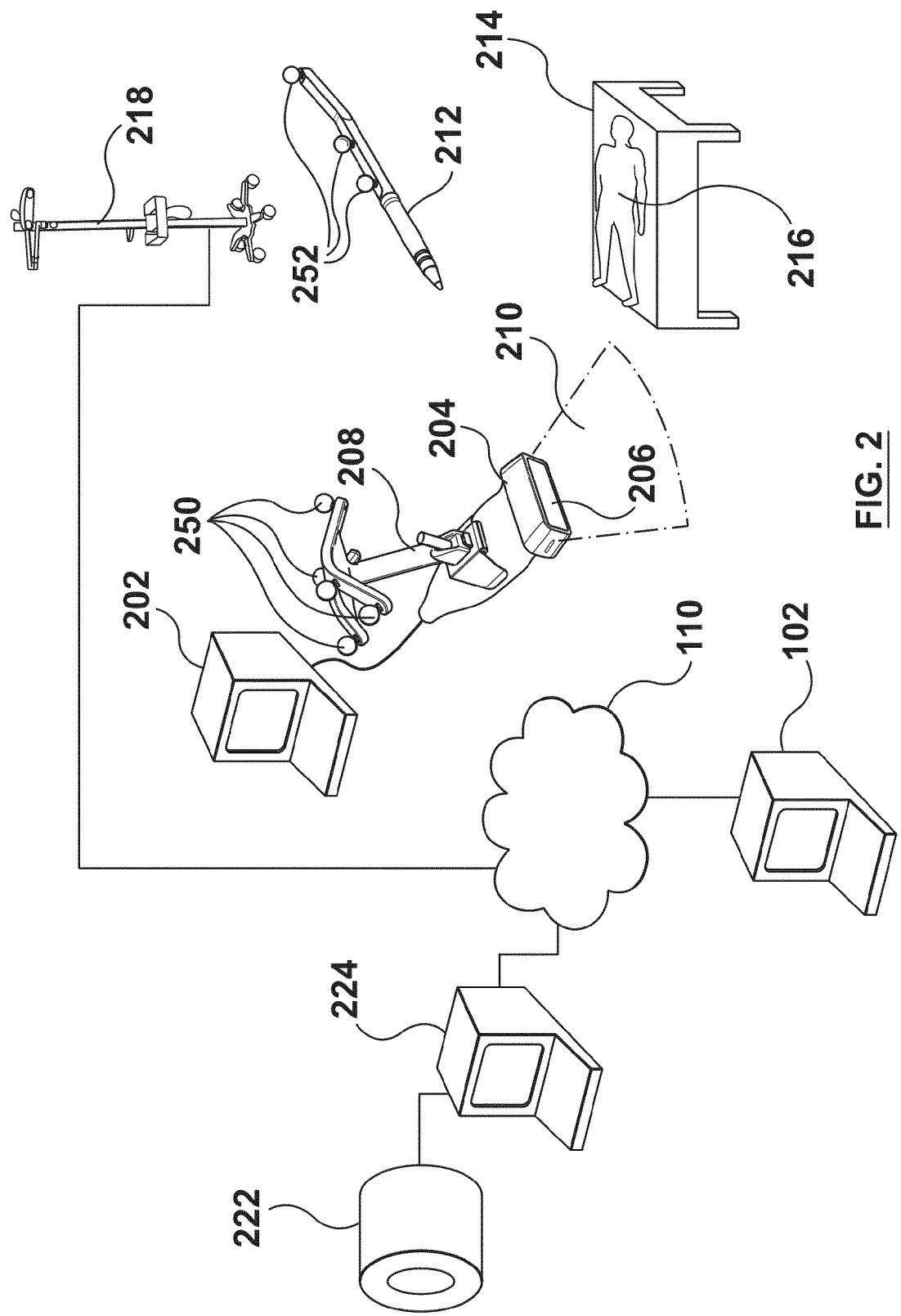
FIG. 2 shows an embodiment of a system for dynamically transforming a displayed MRI image.

With reference to FIG. 2, an embodiment of system 100 for MRI and ultrasound imaging is shown. In the embodiment shown, MRI imaging system 106 comprises MRI imager 222 and MRI workstation 224. MRI imager 222 is an MRI magnet or other MRI imaging device and is in communication with MRI workstation 224 for obtaining an MRI image of a tissue of interest of patient 216.

MRI imager 222 and MRI workstation 224 can be any known MRI imaging system, and skilled persons will understand that, in other embodiments, other 3D imaging systems can be used in place of MRI imager 222 and MRI workstation 224, generating alternative 3D images that can be used instead of an MRI image.

MRI workstation 224 is connected to communication network 110 for transmitting the MRI image obtained during MRI imaging, or any other relevant information and/or data to other workstations or networking devices connected to communication network 110.

The MRI image obtained is stored locally on MRI workstation 224 and is transmitted to navigation system 102 via communication network 110; however, skilled persons will understand that navigation system 102 can access the resulting MRI image remotely via communication network 110 from MRI workstation 224 or, in some embodiments, the resulting MRI image can be stored on a network server connected to communication network 110 which can transmit the MRI image to navigation system 102 or can provide remote access to the resulting MRI image. In other embodiments, skilled persons will understand that the MRI image can be stored on a transportable storage medium at MRI workstation 224, such as a CD-ROM, flash drive or diskette, and loaded into navigation system 102. Navigation system 102 can reconstruct and display the MRI image into a 3D image of the tissue that was imaged during the MRI imaging process. The displayed MRI image can be transformed by navigation system 102 to view the MRI image at any plane and any slice position.

Skilled persons will understand that the MRI image obtained can be transmitted to navigation system 102 at any point in time and is not necessarily transmitted immediately after MRI workstation 224 has obtained the completed MRI image. Instead, the MRI image can be transmitted to navigation system 102 on the request of navigation system 102 or by a user using a transportable media device.

In the embodiment shown in FIG. 2, ultrasound imaging system 104 comprises ultrasound probe 204 and ultrasound workstation 202. Ultrasound workstation 202 is connected to ultrasound probe 204 for obtaining an ultrasound image of patient 216. Ultrasound probe 204 has ultrasound transducer 206 for transmitting sound waves and receiving the reflected sound waves within field of view 210. Ultrasound probe 204 is used to obtain an ultrasound image of a tissue of patient 216 who is positioned on examination table 214; however skilled persons will appreciate that patient 216 may be positioned in any convenient location to obtain an ultrasound image of a tissue of interest and on any support structure, for example a chair.

Ultrasound probe 204 provides data to ultrasound workstation 202 which interprets the data to generate and display an ultrasound image of the tissue of patient 216 within the field of view 210 of ultrasound probe 204. In the embodiment shown, ultrasound workstation is a stand-alone workstation; however, in some embodiments, ultrasound workstation 202 can be connected to communication network 110 and can transmit the ultrasound image to navigation system 102 via communication network 110, or in alternative embodiments, through a transportable media device, such as a CD-ROM, flash drive, diskette or other similar transportable media device. Additionally, skilled persons will appreciate that navigation workstation 102 can access the ultrasound image remotely via communication network 110 or in some embodiments, the ultrasound image can be stored on a network server in communication with communication network 110 and navigation system can remotely access, or obtain a copy, from such network server via communication network 110.

In the embodiment shown, tracking system 108 comprises optical camera 218 and a plurality optical transmitters; however, skilled persons will understand that alternative tracking systems can be used, such as RF magnetic tracking systems. Optical camera 218 is connected to communication network 110 for transmitting the three dimensional coordinate data of the plurality of optical transmitters to navigation system 102 in the tracker co-ordinate space. Optical camera 218 monitors the position and orientation of ultrasound probe 204 by tracking ultrasound transmitters 250 and transmits this data to navigation system 102 via communication network 110. Skilled persons will appreciate that in some alternative embodiments, optical camera 218 can be connected directly to navigation system 102 via a direct communication link, which may be a physical communication link or a wireless communication link.

In the embodiment shown, ultrasound probe 204 is removably engaged to ultrasound tracker 208 which has ultrasound transmitters 250 that are tracked by optical camera 218 in the tracker co-ordinate space. Skilled persons will appreciate that while in the embodiment shown, ultrasound transmitters 250 are optical transmitters tracked by optical camera 218, other transmitter-receiver systems can be used. For example, in other embodiments, RF transmitters and receivers can be used to track the position and orientation of ultrasound probe 204 in the tracker co-ordinate space. Additionally, skilled persons will appreciate that other orientations and positions of ultrasound transmitters 250 on ultrasound tracker 208 can be used to provide position and orientation information detectable by optical camera 218 and transmitted to navigation system 102. Skilled persons will understand that the use of transmitters that are removably connected to ultrasound probe 204 can tend to provide the ability to configure any ultrasound probe with any shape of transducer, such as linear transducers, curvilinear transducers and array and phased array transducers.

Figure 3:
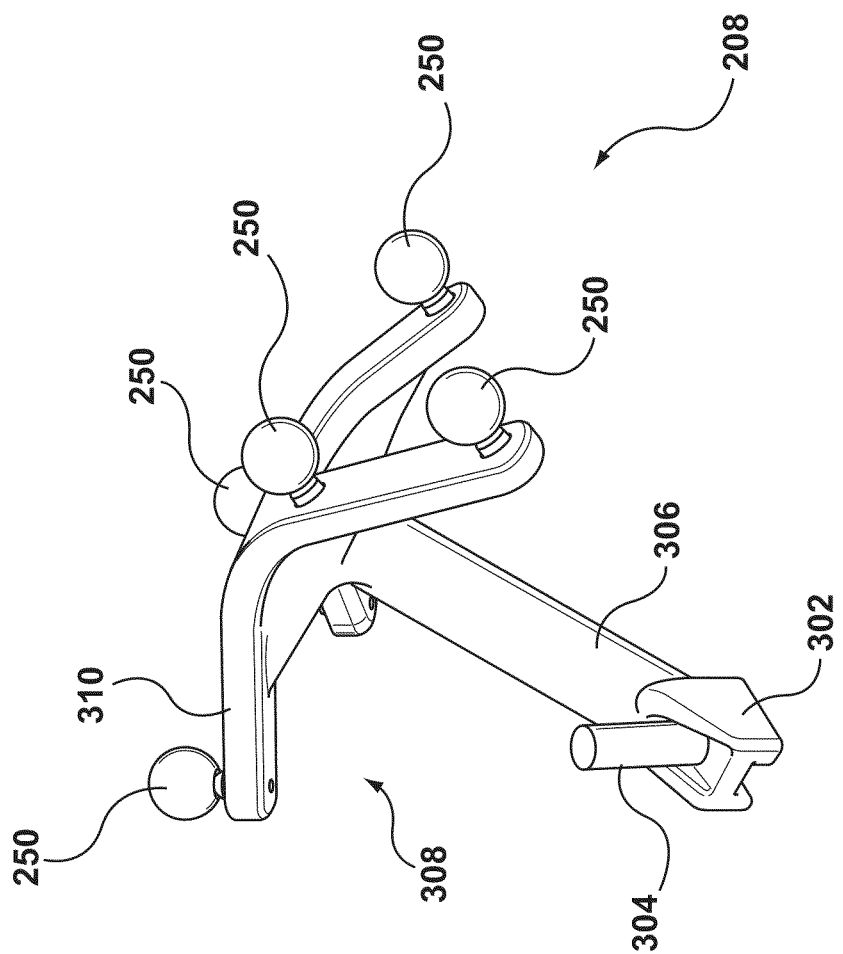
FIG. 3 shows an embodiment of an ultrasound tracker for removable engagement with an ultrasound probe in the system shown in FIG. 2.
Figure 4:
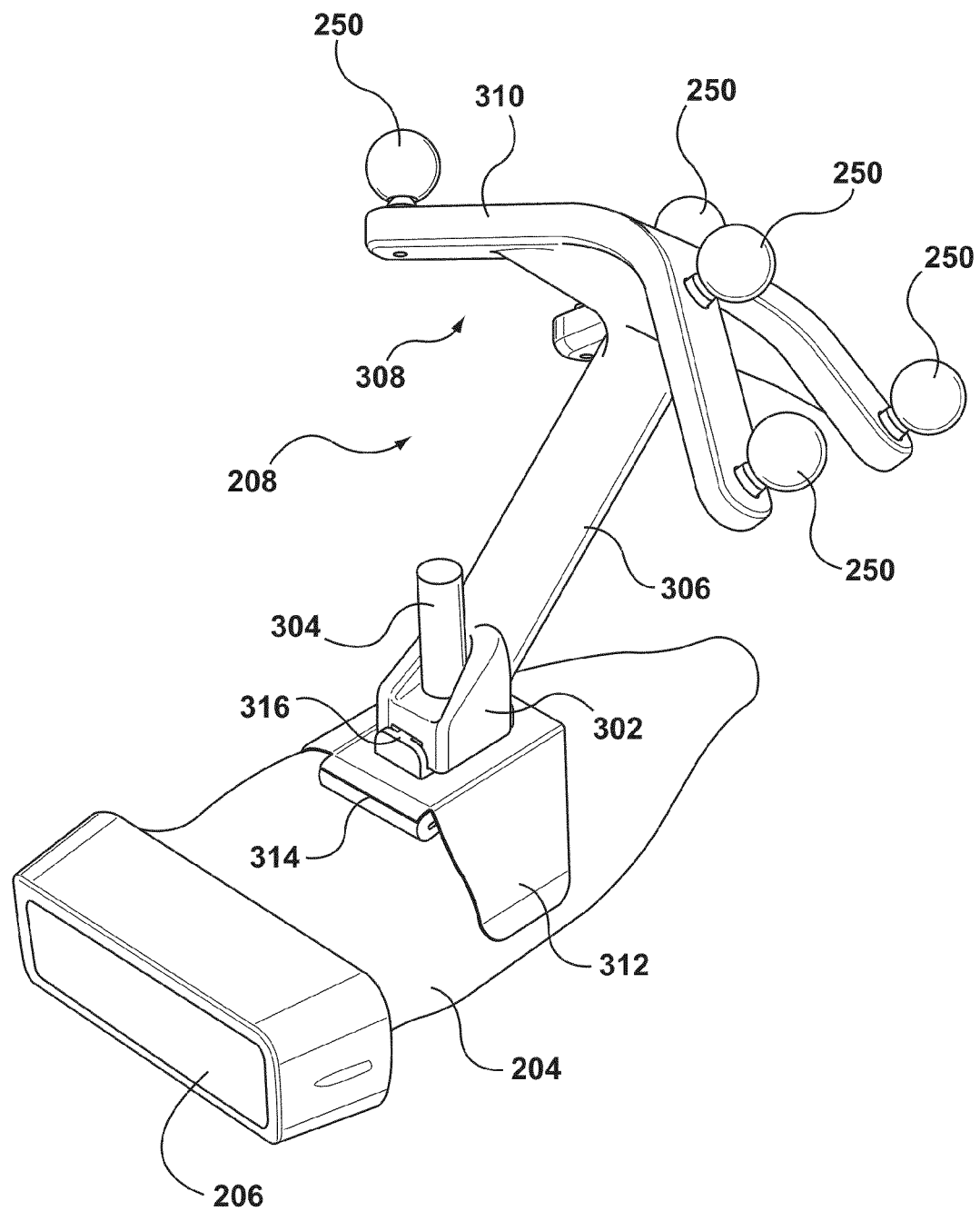
FIG. 4 shows an embodiment of the ultrasound tracker shown in FIG. 3 engaged to an ultrasound probe.

With additional reference to FIGS. 3 and 4, an embodiment of ultrasound tracker 208 is shown having extension arm 306 and branches 310 with ultrasound transmitters 250 connected to branches 310 of ultrasound tracker 208. Ultrasound tracker 208 additionally has engagement brace 302 and locking screw 304, engagement brace 302 connectable to ultrasound bracket 314 by slidable connection to engagement bracket 316. Locking screw 304 is turned to lock engagement brace 302 to engagement bracket 316. Ultrasound bracket 314 additionally has connection arms 312 for frictional engagement to ultrasound probe 204 when in use. Skilled persons will appreciate that other mechanical means can be used to maintain the position of ultrasound tracker 208 on ultrasound probe 204.

Referring back to FIG. 2, ultrasound probe 204 is configured to be used with navigation system 102 using stylus 212. Stylus 212 is fitted with stylus transmitters 252 and its position and orientation is received by optical camera 218 in the tracker co-ordinate space. The orientation and position information of stylus 212 is transmitted to navigation system 102 via communication network 110 where it is used to configure ultrasound imaging probe 204 with navigation system 102 so that navigation system 102 can determine the position and orientation of field of view 210 of ultrasound probe 204 in the tracker co-ordinate space.

Figure 5:
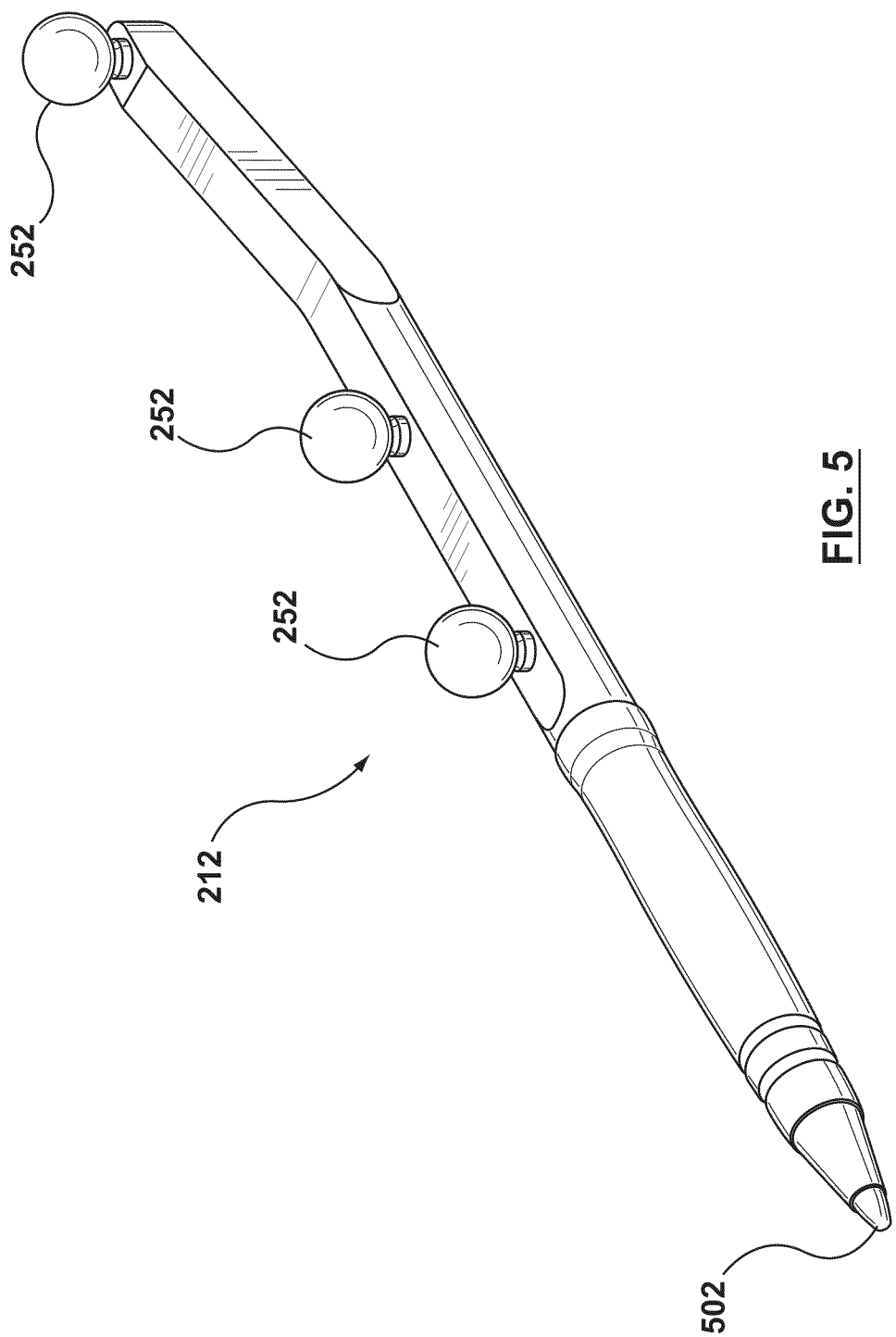
FIG. 5 shows an embodiment of a stylus for use configuring the ultrasound probe with the navigation workstation shown in the system shown in FIG. 2.

With additional reference to FIG. 5, an embodiment of stylus 212 is shown, having tip 502 and stylus transmitters 252 arranged at locations on stylus 212 to provide position and orientation data of stylus 212 to camera 218. Skilled persons will appreciate that stylus 212 is an exemplary embodiment of a configuration tool that can be used to configure ultrasound probe 204 with navigation system 102 so that navigation system 102 can determine field of view 210 of ultrasound probe 204. Other configuration tools may be used.

In use, navigation system 102 is set to a configuration mode, where an operator can use stylus 212 to configure ultrasound probe 204 with navigation system 102. In some embodiments, tip 502 of stylus 212 can be touched to predetermined points on transducer 206 to configure ultrasound probe 204 with navigation system 102. Navigation system 102 can use a pre-computed 4×4 stylus calibration matrix to determine the co-ordinates of stylus tip 502 in the tracker co-ordinate space given the tracked position and orientation of the stylus transmitters 252. For example, in such embodiments, a user acknowledges with navigation system 102 that stylus 212 is in contact with a first corner of the face of transducer 206 on navigation system 102, and the position of the first corner of the face of transducer 206 is recorded by navigation system 102 in tracker co-ordinate space. In such embodiments, the user moves stylus 212 to each corner of the face of transducer 206 and acknowledges such corner on navigation system 102, and at the conclusion of acknowledging and recording the position of each corner of transducer 206 in the tracker co-ordinate space, navigation system 102 can configure ultrasound probe 204 by determining the geometric relationship between field of view 210 and ultrasound tracker 208. This geometric relationship may take the form of a linear affine transformation, which may be represented and stored in a 4×4 affine transformation matrix. Navigation system 102 can additionally perform an error check on the configuration and can reject the configuration of ultrasound probe 204 if, for example, the user improperly positioned stylus 212 during the configuration procedure, or if, for example, the user improperly acknowledged the position of stylus 212 during the configuration procedure.

In other embodiments, field of view 210 of ultrasound probe 204 can be configured in navigation system 102 by accessing a database of pre-configuration data based on the brand and type of ultrasound probe being configured. In such embodiments, it may be desirable to position ultrasound tracker 208 in a predetermined position on ultrasound probe 204 based on the specific brand and type of ultrasound probe 204 being configured. This pre-configuration data can also be used when field of view 210 of ultrasound probe 204 is configured using stylus 212, or another configuration tool, to error check the calculated geometric relationship between field of view 210 and ultrasound tracker 208. For example, the determined geometric transformation can be compared to the pre-configuration data to determine if it is within a tolerance value, and if not, navigation system 102 may prompt the user to re-configure ultrasound probe 204.

Navigation system 102 can be configured to transform the position and orientation of the field of view of the ultrasound probe from the tracker co-ordinate space to a position and orientation in the MRI image, for example, to DICOM co-ordinates. This can be accomplished by tracking the position and orientation of field of view 210 of ultrasound probe 204 based on the tracked position of ultrasound transmitters 250, transmitting this positional information in the tracker co-ordinate space to navigation system 102 and relating this positional information to the MRI co-ordinate system. For example, in some embodiments, this configuration can occur by a user selecting an anatomical plane within the MRI image and a user can then align ultrasound probe 204 so that field of view 210 is in the selected anatomical plane. Once alignment is achieved, the associated tracker co-ordinate space co-ordinates of the ultrasound image can be captured. Registration of the anatomic axes (superior-inferior (SI), left-right (LR) and anterior-posterior (AP)) between the MRI image and the tracker co-ordinate space can be determined from the relative rotational differences between the tracked ultrasound field of view orientation and the selected anatomical plane.

A landmark in the MRI image can be selected using, for example, a user interface that permits the user to select the landmark. In some embodiments, the landmark can be an internal tissue landmark, such as tendon, bone, veins or arteries, and in other embodiments, the target can be an external landmark, such as a fiducial skin marker or external landmark, such as a navel or nipple. The same landmark selected in the MRI image can be located with ultrasound probe 204, and upon location, a mechanism can be provided for capturing coordinates of the representation of the target in the tracker co-ordinate space. The relative differences between the coordinates of the target and the co-ordinates of the MRI image and the located target in the tracker co-ordinate space are used to determine the translational parameters between the two co-ordinate spaces. The plane orientation information can be combined with the previously acquired translation parameters to provide a complete 4×4 transformation matrix which can co-register the tracker space and MRI space co-ordinate systems.

In some embodiments, navigation system 102 can display additional MRI images in separate frames or positions on a display screen. For example, the MRI image can be displayed with a graphical representation of field of view 210 of ultrasound probe 204 wherein the graphical representation is positioned to represent the position and orientation of field of view 210. In alternative embodiments, a graphical representation of field of view 210 may be displayed in a plane normal to field of view 210 and navigation system 102 can show a 3D MRI image of the tissue of the patient, but rotated and oriented to show the position and orientation of the tissue of patient 216 relative to field of view 210 of ultrasound probe 204.

In other embodiments, the ultrasound image being displayed by ultrasound imaging system 104 can be superimposed on the slice of the MRI image being displayed by navigation system 102 such that a user can view both the MRI and ultrasound images simultaneously, overlaid on the same display. In such embodiments, navigation system 102 can enhance certain aspects of the ultrasound or MRI images to increase the quality of the resulting combined image.

Figure 6:
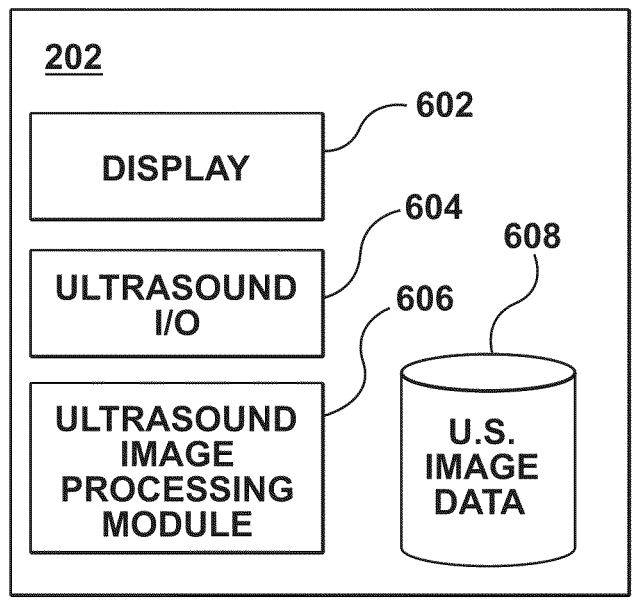
FIG. 6 shows an embodiment of the ultrasound workstation shown in FIG. 2.

With reference to FIG. 6, an embodiment of ultrasound workstation 202 is shown. Ultrasound workstation 202 has display 602, ultrasound I/O 604, ultrasound image processing module 606 and ultrasound image data 608. Ultrasound I/O 604 communicates with ultrasound probe 204, such that transducer 206 produces sound waves that penetrate the tissue of patient 216 and reflect off internal tissue elements in patient 216 the reflected sound waves being received by transducer 206 and transmitted to and received by ultrasound I/O 604.

The ultrasound data received is processed by ultrasound image processing module 606 to generate an ultrasound image of the tissue of patient 216 in field of view 210 of ultrasound probe 204. The resulting image is stored as ultrasound image data 608 and displayed on display 602. Display 602 shows an ultrasound image of the tissue of patient 216 in field of view 210 of ultrasound probe 204.

In some embodiments, ultrasound workstation 202 can communicate via communication network 110 to transmit data, such as ultrasound image data 608, to other nodes or network elements, such as navigation system 102, in communication with communication network 110. Skilled persons will appreciate that ultrasound workstation 202 may consist of other configurations and may include additional elements that enable ultrasound workstation 202 to obtain and display an ultrasound image of the tissue of patient 216 in field of view 210 of ultrasound probe 204.

Figure 7:
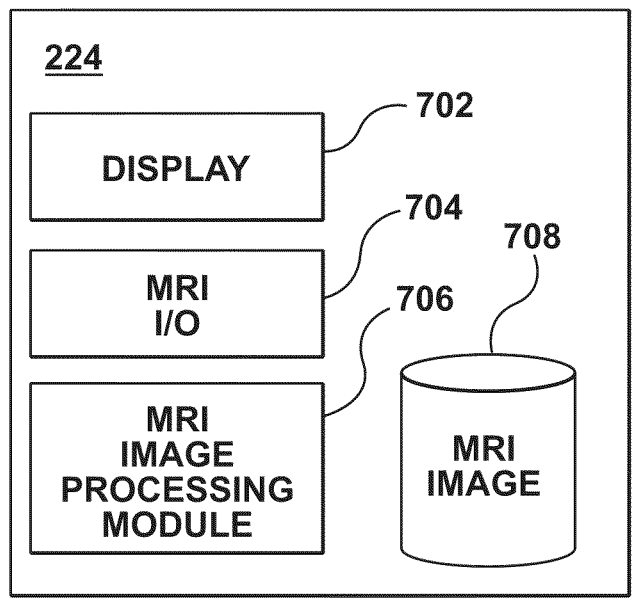
FIG. 7 shows an embodiment of the MRI workstation shown in FIG. 2.

With reference to FIG. 7 an embodiment of MRI workstation 224 is shown having display 702, MRI I/O 704, MRI image processing module 706 and MRI image data 708. MRI I/O 704 communicates with MRI imager 222 for sending and receiving excitation signals during the MRI imaging process. MRI image processing module 706 receives signals from MRI I/O 704 and detects and processes these signals to generate MRI image data 708. MRI image data 708 is additionally processed by MRI image processing module 706 to display an MRI image of the tissue of patient 216 on display 702 which can be reformatted and repositioned using user interface devices, for example a mouse, keyboard, touch screen, or other similar user interface device, to display MRI image 708 at any plane and any slice position. Skilled persons will appreciate that MRI workstation 224 may consist of other configurations and may include additional elements that enable MRI workstation 224 to obtain and display an MRI image of the tissue of patient 216.

Figure 8:
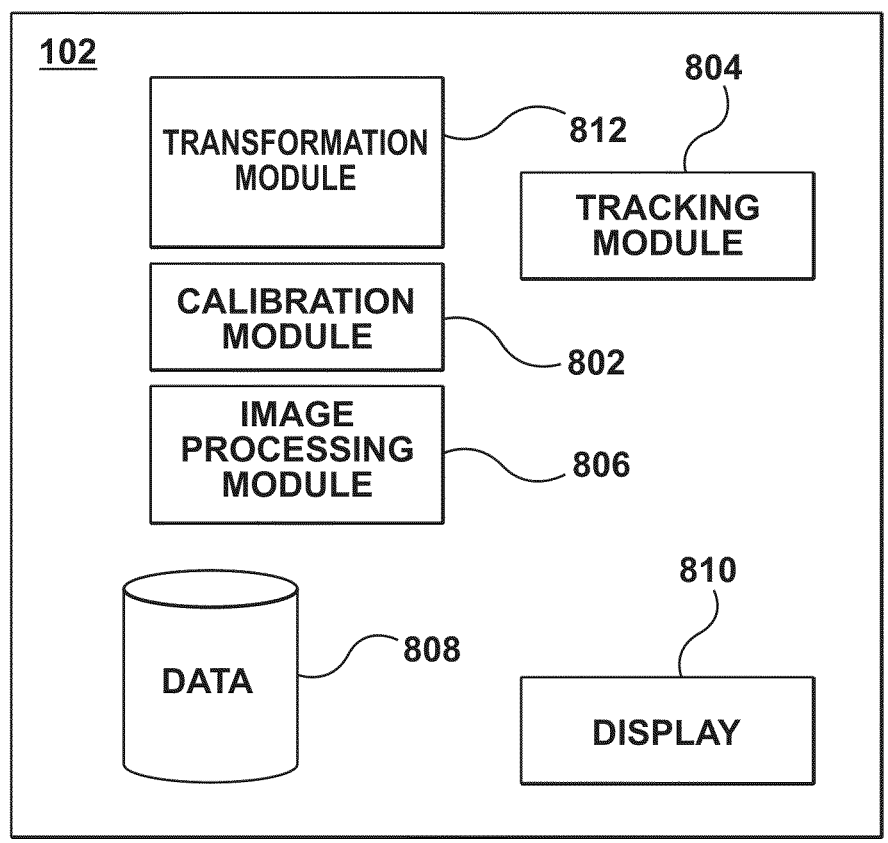
FIG. 8 shows an embodiment of the navigation system shown in FIG. 2.
Figure 9:
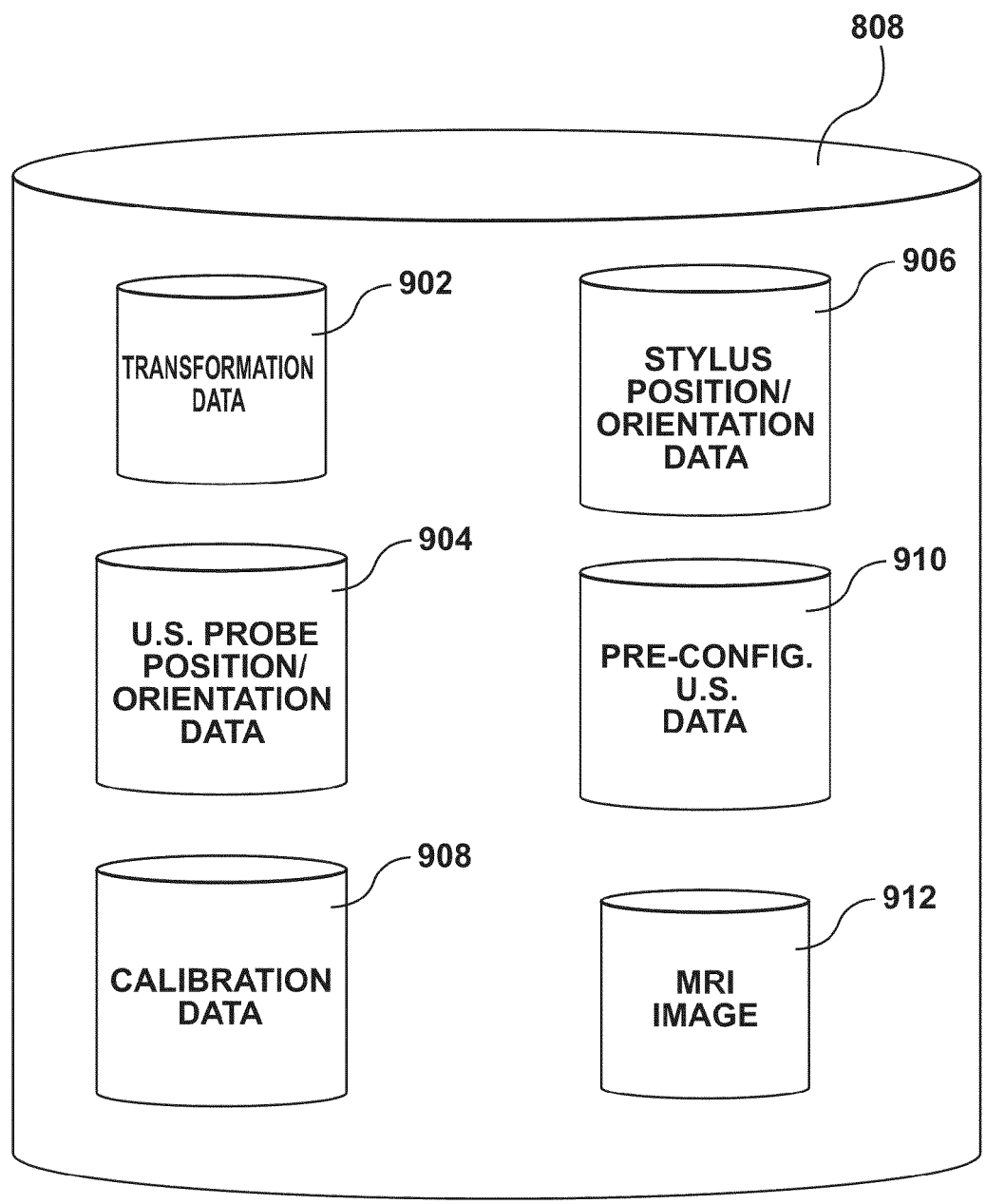
FIG. 9 shows an embodiment of the data of the navigation system shown in FIG. 8.

With reference to FIG. 8, an embodiment of navigation system 102 is shown. Navigation system 102 has calibration module 802, tracking module 804, image processing module 806, transformation configuration module 812, navigation system data 808, and display 810. With additional reference to FIG. 9, an embodiment of navigation system data 808 is provided and comprises transformation data 902, ultrasound probe position and orientation data 904, stylus position and orientation data 906, calibration data 908, pre-configuration ultrasound data 910, MRI image data 912.

Figure 11:
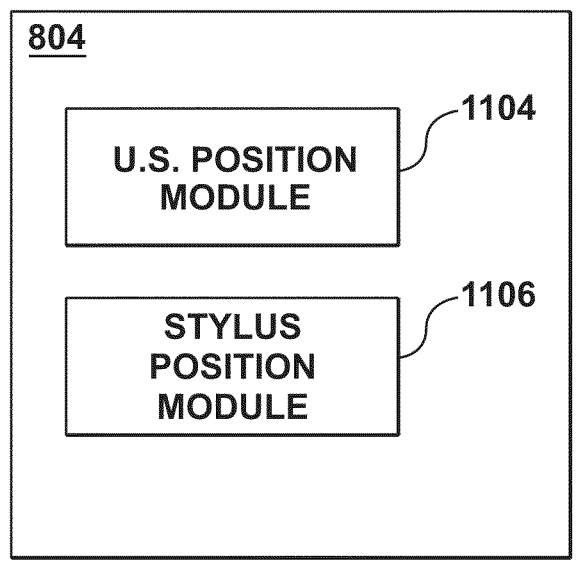
FIG. 11 shows an embodiment of the tracking module of the navigation system shown in FIG. 8.

With additional reference to FIG. 11, an embodiment of tracking module 804 is shown. Ultrasound position module 1104 receives information from optical camera 218 through communications network 110 and interprets that information to generate ultrasound position and orientation data 904 in the tracker co-ordinate space. Stylus position module 1106 receives information from optical camera 218 through communications network 110 and interprets that information to generate stylus position and orientation data 906 in the tracker co-ordinate space. Stylus position module 1106 can additionally determine the physical position and orientation of tip 502 of stylus 212 based on a pre-configured 4×4 stylus transformation matrix based on the position of stylus transmitters 252 on stylus 212.

It will be understood by those skilled in the art that, while this embodiment shows an optical transmitter-receiver system, other transmitter-receiver devices can be used to generate ultrasound probe position and orientation data 904 and stylus position and orientation data 906, such as RF transmitter receiver systems. Additionally skilled persons will understand that the tracking system may interpret and process the data received directly and transmit position and orientation data to navigation system 102.

Calibration module 802 calibrates field of view 210 of ultrasound probe 204 with navigation system 102 using ultrasound probe position and orientation data 904 and stylus position and orientation data 906 to generate and store calibration data 908. With additional reference to FIG. 10, an embodiment of calibration module 802 is shown and consists of calibration configuration module 1002, error correction module 1004 and pre-configuration module 1006. Calibration configuration module 1002 determines the calibration matrix used to transform ultrasound position and orientation data 904 in the tracker co-ordinate space into coordinates representing the position and orientation of field of view 210 in MRI image 912.

Figure 13:
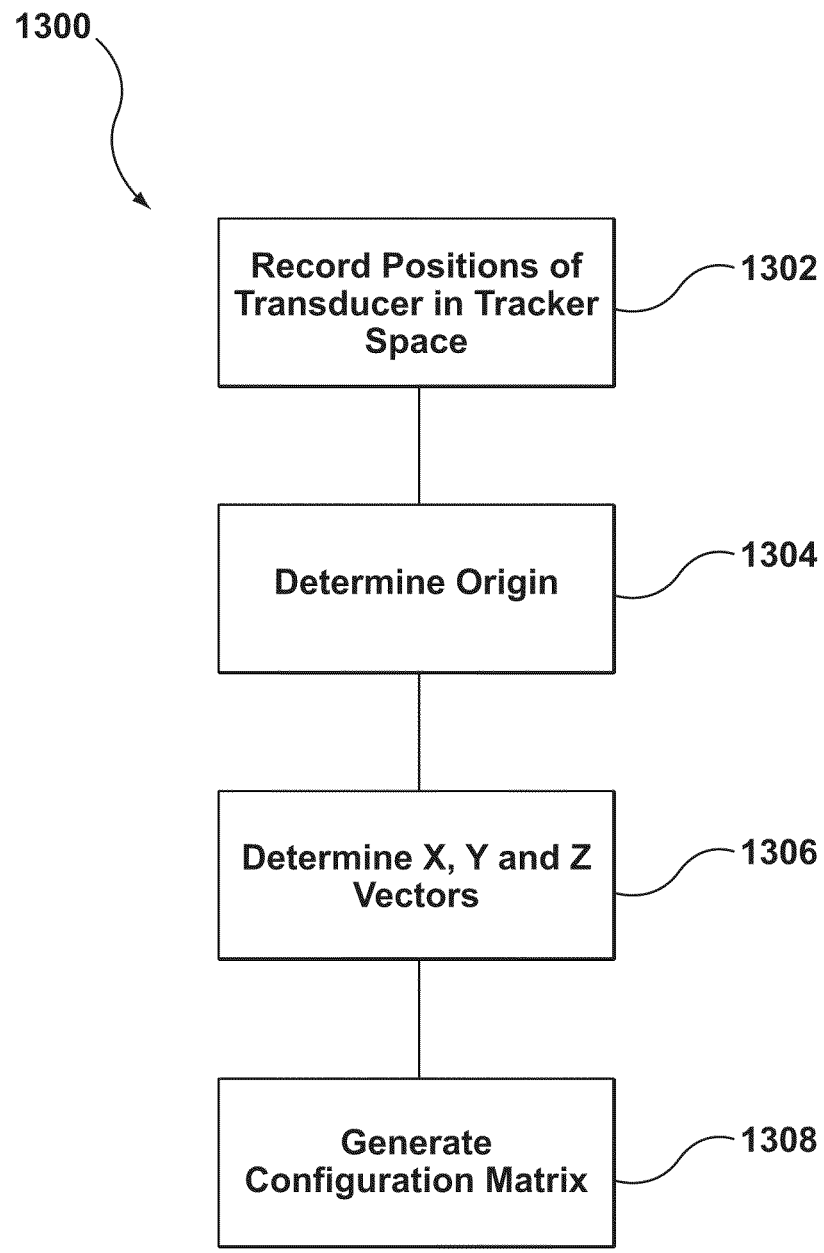
FIG. 13 shows an embodiment of a method for configuring the ultrasound probe shown in FIG. 2 with the navigation workstation shown in FIG. 2.

With additional reference to FIG. 13, an embodiment of a method of calibration implemented by calibration module 1002 is shown. At 1302, stylus 212 is used to select the four corner points of the face of transducer 206 and navigation system 102 can store the tracked stylus position and orientation data 906 relative to the co-ordinate frame of ultrasound transmitters 250. In some embodiments, where all of the column vectors determined below are derived from these initial corner point selections, the computed column vectors can be defined in the co-ordinate frame of ultrasound transmitters 250. In some embodiments, navigation system 102 provides a visual prompt to a user and indicates which corner of the face of transducer 206 should be selected by stylus 212; however in alternative embodiments the user can select any corner point and may not be prompted for a specific corner point. A user touches tip 502 of stylus to the specified corner point of the face of transducer 206 and provides a user acknowledgement to navigation system 102, typically through a user interface device, such as, a keyboard, mouse, or touch screen. Using a pre-computed 4×4 stylus calibration matrix (used to determine the co-ordinates of stylus tip 502 relative to the tracked position of stylus transmitters 252) navigation system 102 can store the tracked position of stylus tip 502 in stylus position and orientation data 908 relative to the co-ordinate frame of ultrasound transmitters 250.

At 1304, calibration configuration module 1002 performs a principle components analysis using the four corner points as inputs. The origin (O) of the co-ordinate frame of transducer 206 is located at the mean of the corner points stored in stylus position and orientation data 906. The mean is calculated as the vector sum of the four corner points divided by a scalar factor of 4.

At 1306, calibration configuration module 1002 continues the principle components analysis and determines the Z, Y, and X axes of the co-ordinate frame defined by transducer 206 which can be defined as the 1st, 2nd and 3rd principle components of the principle components analysis. A convention can be defined to reproducibly assign the positive "sense" of each of the X, Y and Z axes. In some embodiments, when the X, Y and Z axes, as well as the origin (O) are determined in the co-ordinate frame defined by ultrasound transmitters 250, at

1308, the 4×4 configuration matrix can be determined as [X Y Z O; 0 0 0 1] where X, Y, Z and O are three element column vectors, which can be used to transform tracked position and orientation information in the co-ordinate frame of transducer 206 into the tracker co-ordinate space.

Figure 14:
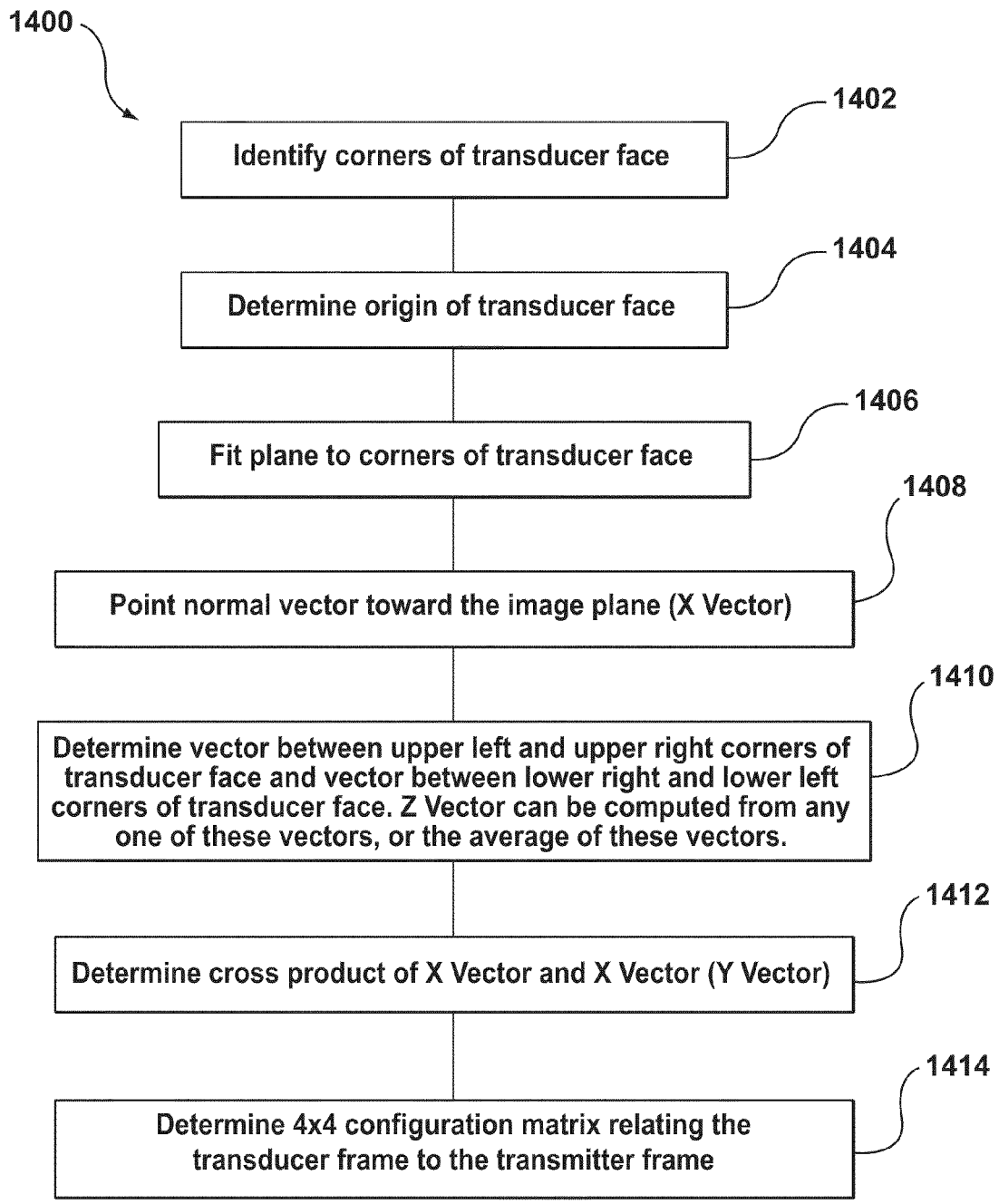
FIG. 14 shows another embodiment of a method for configuring the ultrasound probe shown in FIG. 2 with the navigation workstation shown in FIG. 2.

With reference to FIG. 14, an alternative embodiment of a method of calibration implemented by calibration configuration module 1002 is shown. At 1402, stylus 212 is used to select the four corner points of the face of transducer 206. Using a pre-computed 4×4 stylus calibration matrix (used to determine the co-ordinates of stylus tip 502 relative to the tracked position of stylus transmitters 252) navigation system 102 can store the tracked position of stylus tip 502 in stylus position and orientation data 908 relative to the co-ordinate frame of ultrasound transmitters 250. In some embodiments, the co-ordinates of the four corner points can be defined as the upper-left, upper-right, lower-left and lower-right, which can be three dimensional column vectors specified in the co-ordinate frame of ultrasound transmitters 250.

In some embodiments, display 810 of navigation system 102 provides a visual prompt to a user and indicates which corner of the face of transducer 206 should be selected by stylus 212; however in alternative embodiments the user can select any corner point and may not be prompted for a specific corner point. A user touches tip 502 of stylus 212 to the specified corner point of the face of transducer 206 and provides a user acknowledgement to navigation system 102, typically through a user interface device such as a keyboard, mouse, or touch screen. At each user acknowledgement, tracking module 804 records the position and orientation of tip 502 of stylus 212 determined from the position and orientation of stylus transmitters 252 on stylus 212. Each corner point is stored in stylus position and orientation data 906. In some embodiments, the user may select each corner point of the face of transducer multiple times and tracking module 804 averages the multiple selections of the same corner point, which can tend to reduce errors due to noise and user selection variability.

At 1404, calibration configuration module 1002 determines the origin (O) of the co-ordinate frame of transducer 206 which is located at the vector sum of the corner points stored in stylus position and orientation data 906, divided by a scalar factor of 4, specified in co-ordinates in the co-ordinate frame of ultrasound transmitters 250. At 1406, calibration configuration module 1002 uses the four corner points to determine a plane representing the face of ultrasound probe 202.

At 1408, calibration configuration module 1002 determines the normal of the plane representing the face of ultrasound probe 206, which corresponds to the X vector for the co-ordinate frame of transducer 206, meaning the vector along the axis of ultrasound probe 206. Additionally, at 1406, calibration configuration module 1002 performs a check to see if the sense of vector X points toward the image plane rather than towards the handle of ultrasound probe 204, which can be done by calculating the dot product of the X vector and any point on the face of transducer 206 (including O or any of the 4 corner points) wherein if the dot product is positive, the X vector is pointing towards the image plane, and if not, the X vector may be negated so that it is pointing towards the image plane.

At 1410, calibration configuration module 1002 determines the vector defined by the upper left and upper right corner points and additionally determines the vector defined by the lower left and lower right corner points. Calibration configuration module 1002 defines both vectors to be the Z vector, or in some embodiments, may average the two vectors to obtain an estimate of the Z vector.

At 1412, calibration configuration module 1002 determines the Y vector of the co-ordinate frame of transducer 206 which is the cross product of the X and Z vectors. Skilled persons will understand if the Y vector is directed in a negative direction the Y vector can be negated to form a right handed coordinate system. At 1414, calibration configuration module 1002 stores the 4×4 calibration matrix as calibration data 908, wherein the 4×4 calibration matrix can be defined as [X Y Z O, 0 0 0 1], which can be used to transform tracked position and orientation information in the co-ordinate frame of transducer 206 into the tracker co-ordinate space.

Figure 15:
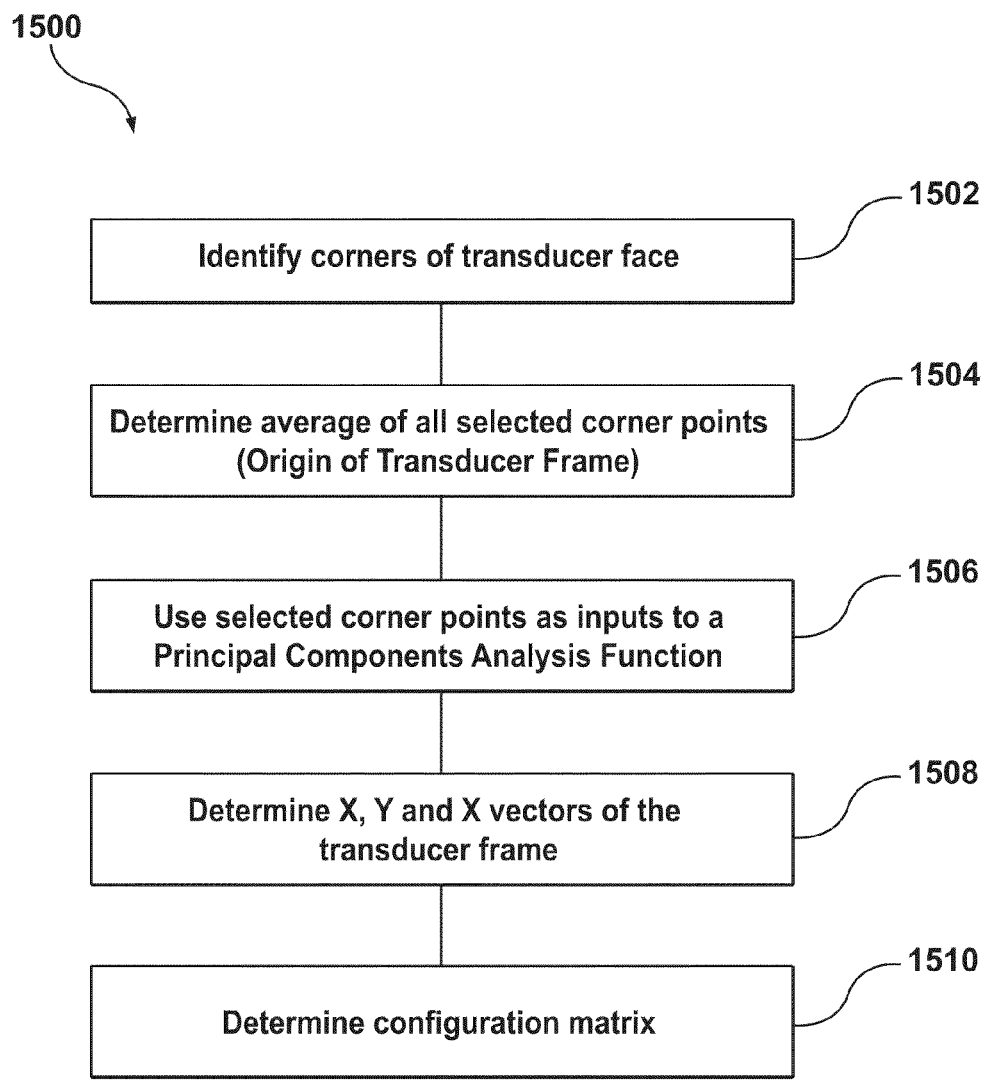
FIG. 15 shows a further embodiment of a method for configuring the ultrasound probe shown in FIG. 2 with the navigation workstation shown in FIG. 2.

With additional reference to FIG. 15, a further embodiment of a method of calibration implemented by calibration configuration module 1002 is shown. It should be noted that for the method shown in FIG. 15, it is assumed that ultrasound transmitters 250 are located on the top surface of ultrasound transducer 204.

At 1502, stylus 212 is used to select the four corner points of the face of transducer 206. Using a pre-computed 4×4 stylus calibration matrix (used to determine the co-ordinates of stylus tip 502 relative to the tracked position of stylus transmitters 252) navigation system 102 can store the tracked position of stylus tip 502 in stylus position and orientation data 908 relative to the co-ordinate frame of ultrasound transmitters 250.

In some embodiments, display 810 of navigation system 102 provides a visual prompt to a user and indicates which corner of the face of transducer 206 should be selected by stylus 212; however in alternative embodiments the user can select any corner point and may not be prompted for a specific corner point. A user touches tip 502 of stylus 212 to the specified corner point of transducer 206 and provides a user acknowledgement to navigation system 102, typically through a user interface device such as a keyboard, mouse, or touch screen. At each user acknowledgement, tracking module 804 records the position and orientation of tip 502 of stylus 212 determined from the position and orientation of stylus transmitters 252 on stylus 212. Each corner point is stored in stylus position and orientation data 906. In some embodiments, the user may select each corner point of the face of transducer multiple times and tracking module 804 averages the multiple selections of the same corner point, which can tend to reduce errors due to noise and user selection variability.

At 1504, calibration configuration module 1002 determines the origin (O) of the co-ordinate frame of transducer 206 which is located at the vector sum of the corner points stored in stylus position and orientation data 906 divided by a scalar factor of 4. The mean vector sum is calculated by the average vector sum of the four corner points.

At 1506, calibration configuration module 1002 uses a principle components analysis function, using the compiled list of all of the selected corner points (xi, yi and zi) as input. The principle components analysis function is insensitive to the order of the input points, so one may not have to know which corner points are which.

At 1508, the calibration configuration module 1002, using the principle components analysis function, outputs three principle components, each representing a three dimensional vector. The first principle component is the direction which explains the most variability in the data and is defined as the Z vector specified in the co-ordinate frame of ultrasound transmitters 250. The second principle component is the direction which is orthogonal to the first principle component and explains the most of the remaining variability in the data is defined as the Y vector specified in the co-ordinate frame of ultrasound transmitters 250. The remaining third principle component is the direction which explains the least variability in the data and is defined as the X vector specified in the co-ordinate frame of ultrasound transmitters 250. Calibration configuration module 1002 determines the correct sense of the Z, Y and X vectors of transducer 206 by determining the dot products of each of vectors X and Y vector with the origin of the co-ordinate frame of transducer 206. The sign of the dot product can be used to insure that the directions of the X, Y, and Z vectors are consistent with a previously defined sign convention. For example, if the previously defined sign convention is that the X vector is positive pointing along the transducer axis toward the ultrasound image plane and away from the transducer handle, then the dot product of X and O should be positive. If this dot product is negative, the X vector can be negated to be consistent with the previously defined sign convention. Analogously, if the previously defined sign convention is that the Z vector points along the direction perpendicular to the ultrasound image plane toward the top of the transducer, the dot product of Z and O should be negative, assuming that the transmitters 250 are also located on the top surface of the transducer. If this dot product is positive, the Z vector can be negated to be consistent with the previously defined sign convention. The direction of the Y vector can then be chosen to provide a right handed co-ordinate system, i.e., Y points in the direction of the negated cross product of X and Z.

At 1508, calibration configuration module 1002 stores the 4×4 calibration matrix as calibration data 908, wherein the 4×4 calibration matrix can be defined as [X Y Z O, 0 0 0 1], which can be used to transform tracked position and orientation information in the co-ordinate frame of transducer 206 into the tracker co-ordinate space.

In other embodiments where ultrasound probe 202 has a curvilinear transducer, additional steps can be performed to compensate for the curvilinear transducer. Using a pre-computed 4×4 stylus calibration matrix (used to determine the co-ordinates of stylus tip 502 relative to the tracked position of stylus transmitters 252) navigation system 102 can store the tracked position of stylus tip 502 in stylus position and orientation data 908 relative to the co-ordinate frame of ultrasound transmitters 250. Using stylus 212, a user can select the approximate center for transducer 206, which can define a 3 dimensional column vector (C) which can be the co-ordinate of the approximate center of the face of transducer 206 in the co-ordinate frame of ultrasound transmitters 206. Vector C, as well as the previously computed O vector, can be projected onto the X axis of the co-ordinate frame of transducer 206. The scalar distance (D) between the projections of the C and O vectors can be computed by taking the absolute value of the difference between the projections of the vectors C and O onto the X vector of the co-ordinate frame of transducer 206. This distance D can be the distance that the co-ordinate frame of transducer 206 can be shifted from the previously computed origin O, along the X axis of the co-ordinate frame of transducer 206. The vector O can be shifted by the distance D along the X axis of the co-ordinate frame of transducer 206 to bring the co-ordinate frame of transducer 206 to the location of the surface of transducer 206. Skilled persons will appreciate that in embodiments using curvilinear transducers that do not compensate with such a correction, the origin O of the co-ordinate frame of transducer 206 will lie behind the face of transducer 206, in the plane of the 4 corners of the face of transducer 206.

Once calibration configuration module 1002 has determined the calibration matrix and has stored the calibration matrix as calibration data 908, error correction module 1004 can perform various tests to determine the accuracy of the transducer calibration with respect to predefined tolerance levels.

In some embodiments, error correction module 1004 determines the best fit plane of each of the corner points and if the perpendicular distance from any corner point to the best fit plane is greater than a predetermined error distance, for example, 2.0 mm, the calibration matrix generated by configuration calibration module 1002 is rejected and the user is prompted to re-configure ultrasound probe 204 with navigation system 102.

In some embodiments, error correction module 1004 computes the center of the face of transducer 206 using the corner points and the distance from each corner point to the computed center is determined. Those distances are compared and if there is a variation between the shortest distance and the longest distance of more than a predetermined value, for example, 2.0 mm, the calibration matrix generated by configuration calibration module 1002 is rejected and the user is prompted to re-configure ultrasound probe 204 with navigation system 102.

In some embodiments, error correction module 1004 projects each of the corner points onto a line that intersects the computed center point of the face of transducer 206 and is perpendicular to field of view 210. The distance between each projection and the computed center point is determined and if there is a variation between the shortest distance and the longest distance of more than a predetermined value, for example, 2.0 mm, the calibration matrix generated by configuration calibration module 1002 is rejected and the user is prompted to re-configure ultrasound probe 204 with navigation system 102.

In some embodiments, error correction module 1004 projects each of the corner points onto a line that is normal to transducer 206 and containing the computed center point of the face of transducer 206. The distance between each projection and the computed center point is determined and if there is a variation between the shortest distance and the longest distance of more than a predetermined value, for example, 2.0 mm, the calibration matrix generated by configuration calibration module 1002 is rejected and the user is prompted to re-configure ultrasound probe 204 with navigation system 102.

In some embodiments, error correction module 1004 determines the angle between the vector that is normal to the face of transducer 206 and the vector extending from tip 502 of stylus 212 as stylus 212 contacts each corner point of the face of transducer 206 during configuration. If any of the calculated angles are greater than a predetermined amount, for example 20 degrees, the calibration matrix generated by configuration calibration module 1002 is rejected and the user is prompted to re-configure ultrasound probe 204 with navigation system 102.

Skilled persons will understand that any or all of the error correction embodiments described above can be implemented by error correction module 1004 after or during calibration by calibration configuration module 1002. Additionally, skilled persons will understand that alternative error correction steps can be implemented to determine if the calibration matrix generated by calibration configuration module 1002 should be rejected and a re-calibration of ultrasound probe 204 with navigation system 102 should occur.

Figure 10:
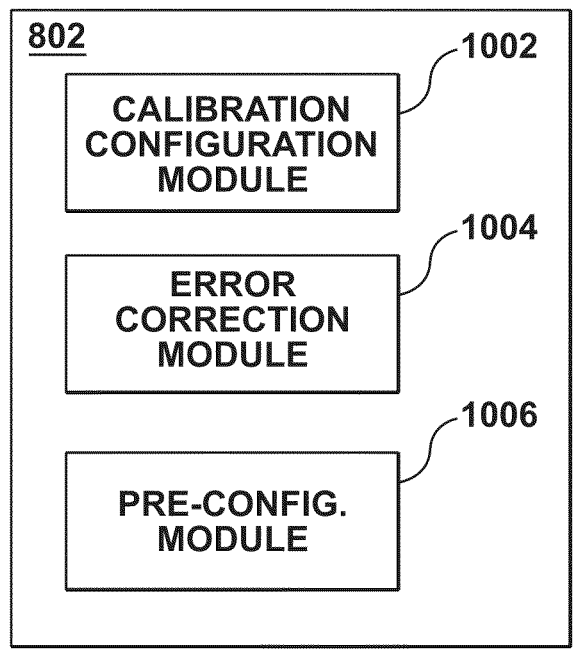
FIG. 10 shows an embodiment of the calibration module of the navigation system shown in FIG. 8.

In the embodiment shown in FIG. 10, calibration module 802 additionally has pre-configuration module 1006, which skilled persons will understand is an optional element in calibration module 802. Pre-configuration module can receive an input from a user, using a user input device such as a keyboard, mouse, touch screen, or other similar user input device, representing a brand or model number of a known ultrasound probe. The calculated dimensions of the ultrasound transducer face can then be compared against the known dimensions of this transducer as determined by previous calibrations or manufacturer mechanical specifications. The transducer calibration can then be rejected by the system if this discrepancy exceeds a pre-specified error threshold.

Figure 16:
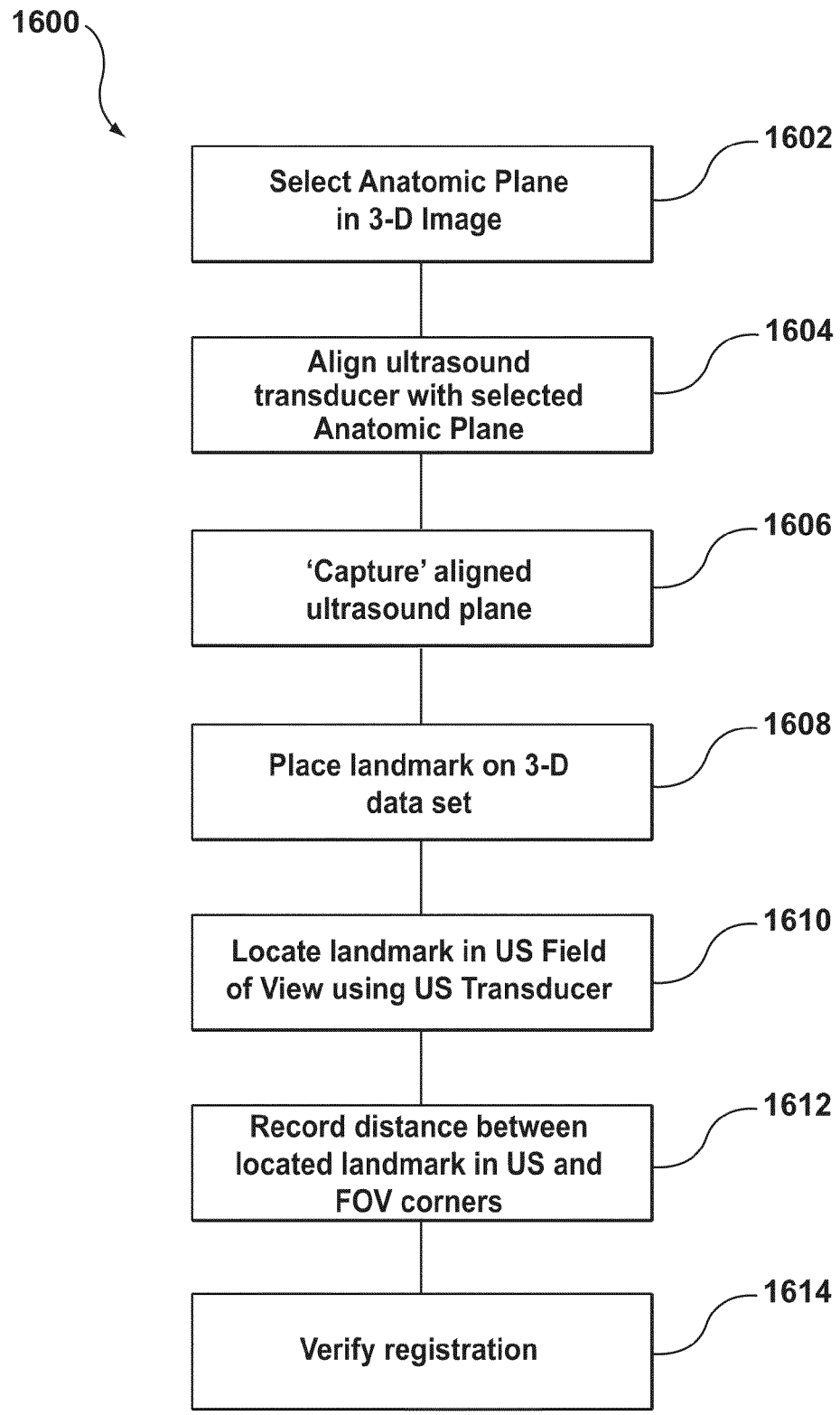
FIG. 16 shows an embodiment of a process for co-registering an ultrasound image with an MRI image.
Figure 17:
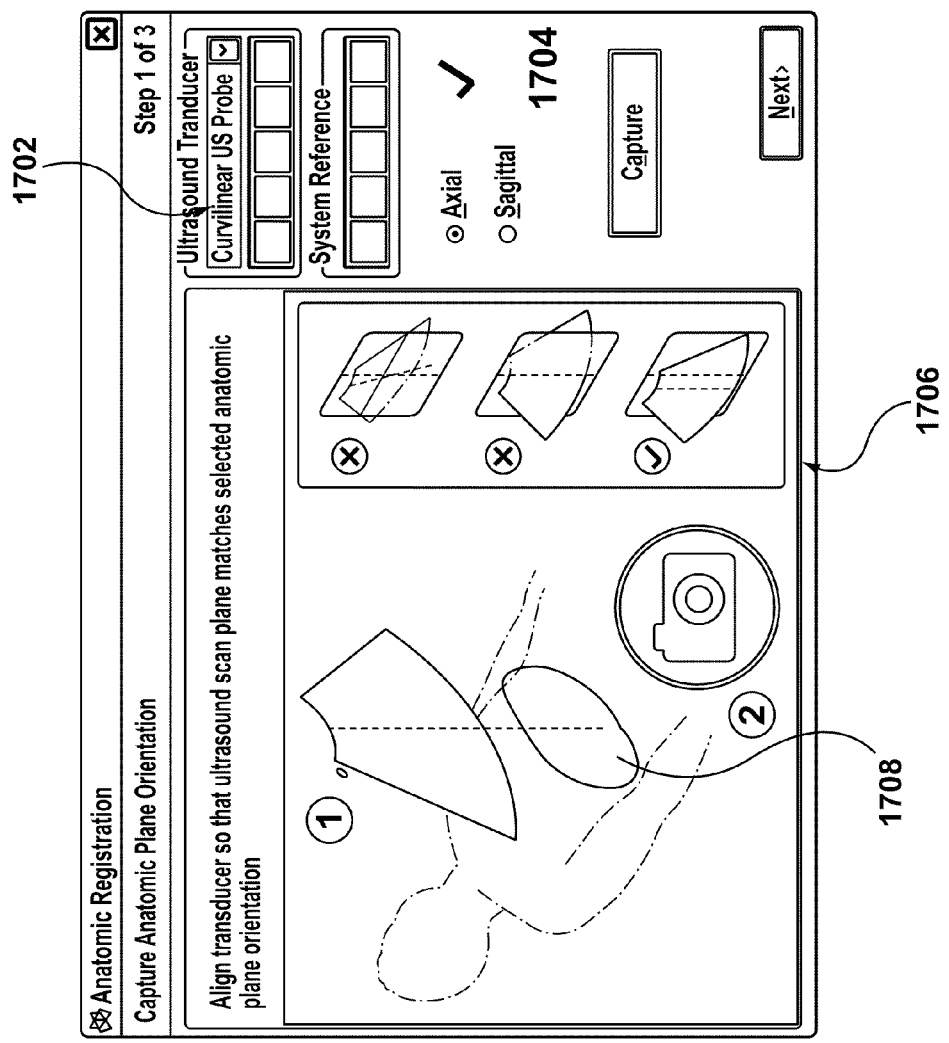
FIG. 17 shows an embodiment of a display screen of a navigation system useful for the selection of an ultrasound probe type when co-registering an ultrasound image with an MRI image.

With reference to FIG. 16, process 1600 is shown, process 1600 being carried out by transformation configuration module 812 to determine a transformation matrix capable of being used to co-register the tracker co-ordinate space with the co-ordinate space of the MRI image. At 1602 the type of ultrasound probe 204 is identified by transformation configuration module 812. This identification can be provided by user input using navigation system, for example using drop down menu 1702 on display 810, as shown in FIG. 17. Using drop down menu 1702 a user can select a type of ultrasound probe, such as a curvilinear ultrasound probe or a flat ultrasound probe.

Additionally, at 1602, a user selects the anatomic plane orientation to position ultrasound probe 204 relative to the tissue of the patient. For example, with additional reference to FIG. 17, a user can select a particular plane of orientation such as axial or sagittal, and a viewing window 1706 and planar image 1708 can be displayed representing field of view 210. Skilled persons will understand that the choice of a particular plane can depend on a variety of factors, such as the particular tissue being imaged. It should be noted that the present invention is not limited in any matter to the selection of any particular plane.

At 1606, the user positioned ultrasound probe 204 in the selected plane of orientation. This alignment can be determined visually by the user or can additionally be determined mathematically by correspondence of desired number of planar points by the navigation system.

At 1608, once alignment is achieved the ultrasound position and orientation as well as the ultrasound image is captured. In some embodiments, a user can select capture selection 1704; however, skilled persons will understand that any user acknowledgement can initiate a capture, such as a foot pedal, keyboard stroke, mouse selection, or any other similar user acknowledgment device. Assuming that ultrasound probe 204 is correctly aligned with the selected anatomic plane orientation, the directions of the anatomic axes (superior-inferior (SI), left-right (LR) and anterior-posterior (AP)) within the tracker co-ordinate space can be inferred by the orientation of ultrasound probe 204. The rotational parameters of the transformation matrix are determined from the rotational offsets between the directions of the anatomical axes in the tracker co-ordinate space and their implicit directions in the MRI image. Once the three rotational parameters of the registration have been calculated, the transformation matrix is completed by calculating three translational parameters to define a six degree of freedom rigid body matrix.

Figure 18:
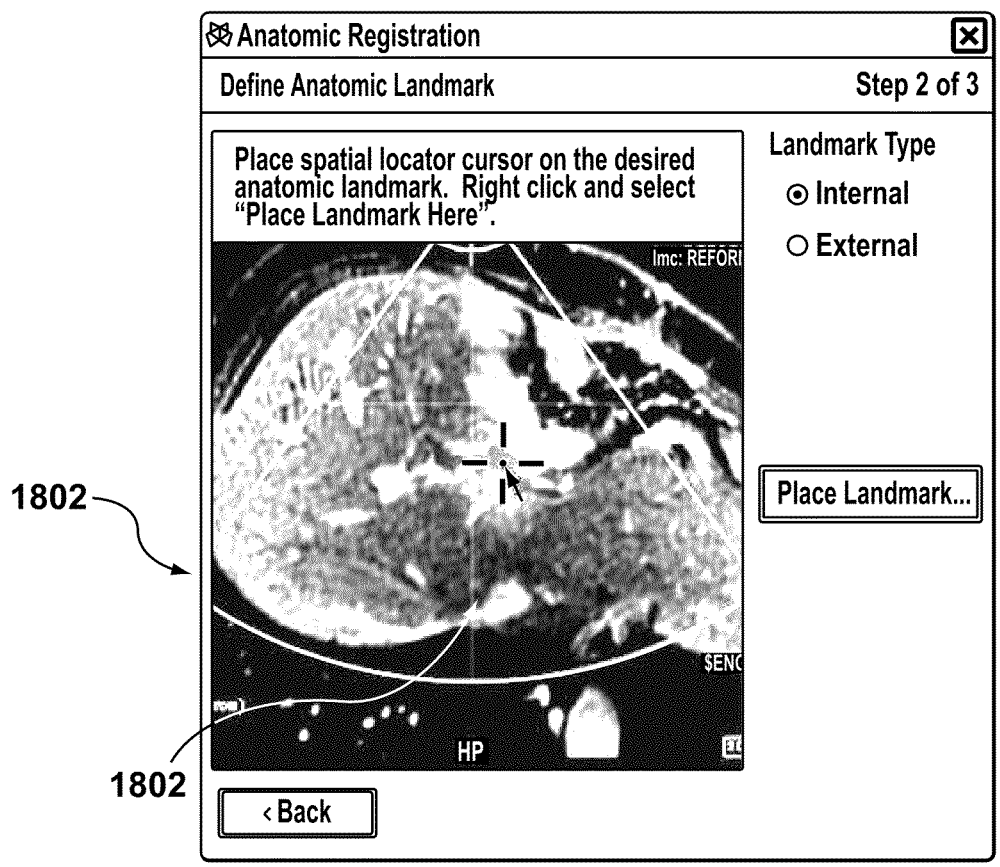
FIG. 18 shows an embodiment of a display screen of a navigation system where a landmark in the tissue is identified.

At 1608, a landmark is identified in the MRI image displayed on display 810 of navigation system 102. For example, with reference to FIG. 18, landmark 1804 can be identified on display 1802 by a user. Skilled persons will understand that while in the embodiment shown the landmark identified is an internal tissue landmark, in other embodiments external anatomical landmarks can be identified. Transformation configuration module 812 stores the co-ordinates of landmark 1804 in the MRI image in transformation data 808. In some embodiments, the landmark can be an internal tissue landmark, such as tendon, bone, veins or arteries, and in other embodiments, the landmark can be an external target, such as a fiducial skin marker or external landmark, such as a navel or nipple.

At 1610, the user positions ultrasound probe 204 so that field of view 210 can detect the internal landmark in the tissue of the patient and the ultrasound image is displayed by ultrasound workstation 202 on display 602. Once the internal landmark is displayed on display 602, the user can freeze the ultrasound image displayed on display 602.

At 1612, the user uses standard measurement tools to measure the distance between the landmark in field of view 210 and the upper right and left corners of field of view 210 of ultrasound probe 204. This distance information can be used to determine the co-ordinates of the landmark in the co-ordinate frame of transducer 206, meaning the distance of the landmark from the center point of the face of transducer 206 along the axial and lateral axes of ultrasound probe 204 and the calibration matrix, described above, can be used to transform these co-ordinates into the tracker co-ordinate space.

Figure 19:
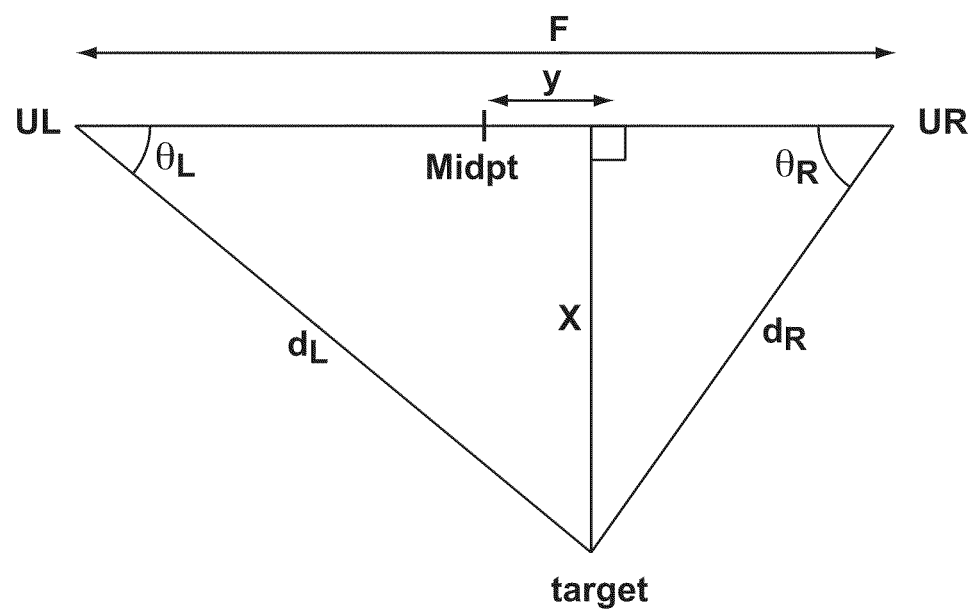
FIG. 19 shows a mathematical model useful in determining the offset of a target in a field of view of a linear ultrasound probe.

With additional reference to FIG. 19, where F is the length of the face of transducer 206, UL and UR are the upper left and upper right corners of field of view 210, for an ultrasound probe with a linear transducer, the axial distance to the internal landmark (x) can be determined in accordance with the following equations:

$$\theta_L = \cos^{-1}\left[\frac{F^2 + d_L^2 - d_R^2}{2Fd_L}\right]$$

Then, assuming right is positive, the distance to the internal landmark (x) can be solved in accordance with the following:

$$x = d_L \sin \theta_L \qquad [1]$$

And the lateral distance from the midpoint to the target (y) can be solved in accordance with the following:

$$y = d_L \cos\theta_L - \frac{F}{2} \qquad [2]$$

With reference to FIG. 20, in an alternative embodiment, where ultrasound probe 204 is a curvilinear probe (the face of transducer 204 being curvilinear), the x offset of target co-ordinates can be determined in accordance with the following, where ROC is the radius of curvature of the curvilinear transducer face:

$$\delta = ROC\left(1 - \cos\left(\frac{\alpha}{2}\right)\right), \qquad [3]$$
$$\text{where } i = ROC \cdot \cos\left(\frac{\alpha}{2}\right) \text{ and } F = 2ROC \cdot \sin\left(\frac{\alpha}{2}\right)$$

In this case the co-ordinates of the selected target relative to the front center of the ultrasound transducer face would be (x−δ, y) where x and y are computed using equations [1] and [2], and δ is computed using equation [3].

Transformation configuration module 812 can compute the transformation matrix, which can convert co-ordinates in the co-ordinate frame of tracking system 108 to co-ordinates in the MRI image. The methods described herein describe the generation of a matrix for transforming co-ordinates in the MRI image to the tracker space co-ordinate frame; however, skilled persons will understand that the geometric transformation from tracker space to MRI space is a linear, invertible operation, and the transformation matrix from tracker space to MRI space is the matrix inverse of the matrix transformation from MRI space to tracker space. The vectors corresponding to the AP, SI and LR directions in the co-ordinate frame of tracking system 108 are determined by the orientation of ultrasound probe 204 when the axial plane is acquired, combined with the previously computed transducer configuration matrix. Skilled persons will understand that in the embodiment shown, the axial plane is the selected plane, however other planes can be selected, such as a sagittal or coronal plane.

The SI direction will correspond to the slice axis of ultrasound probe 204, the LR direction will correspond to the lateral axis of ultrasound probe 204, and the AP direction will correspond to the axial axis of ultrasound probe 204. Unit vectors along each of these directions can be computed in the tracker co-ordinate space using the tracked position and orientation of transducer 206. This can yield three unit vectors in the tracker co-ordinate space that represent the AP, LR and SI directions of the 3d MRI image (which will be referred to as the $AP_{tracker}$, $LR_{tracker}$ and $SR_{tracker}$ vectors. Note that this correspondence assumes that the MRI image was acquired with the patient in a known orientation with respect to the coordinate axes used to define the MRI data acquisition.

The representations of these unit column vectors in the tracker co-ordinate space are placed in the first three columns of a 4×4 transformation matrix (with the fourth row of the 4×4 transformation matrix containing [0 0 0 1]. It should be noted that the order of the $AP_{tracker}$, $LR_{tracker}$ and $SI_{tracker}$ vectors should match the order of the corresponding axes of the MRI image. The sign of these vectors may have to be negated to match the MRI co-ordinate system, for example, if the AP axis is positive in the anterior direction in the MRI image, the $AP_{tracker}$ vector would be negated before being inserted into the transformation matrix to match the MRI co-ordinate system, since ultrasound probe was pointing posteriorly when the plane orientation was captured.

The co-ordinates of the landmark in the tracker space ($x_o$, $y_o$, $z_o$) should be converted into co-ordinates along the AP, LR and SI axes. This can be accomplished by projecting the co-ordinates ($x_o$, $y_o$, $z_o$) onto each of the AP, LR and SI axes in tracker co-ordinate space (which are determined by the transducer orientation when the anatomic plane was selected). The resulting projected co-ordinates of the landmark (referred to as $AP_{proj}$, $LR_{proj}$ and $SI_{proj}$) are now in a co-ordinate system with the same axes as the MRI image (for example DICOM co-ordinates), however, having a different origin (the origin is the origin of the tracker co-ordinate space, not the origin of the MRI/DICOM space). The translation components of the transformation matrix can be computed by taking the difference between the MRI co-ordinates of the selected landmark and the projected co-ordinates of the ultrasound selected landmark, where the offsets can be calculated as $AP_{proj}-AP_{dicom}$, $LR_{proj}-LR_{dicom}$ and $SI_{proj}-SI_{dicom}$. These offsets represent rows 1 to 3 of column 4 in 4×4 transformation matrix, the order reflecting the order of the DICOM dimensions in the MRI image, for example, if the DICOM dimensions are AP, LR and SI, row 1 contains the AP offset, row 2 contains the LR offset, etc. In this embodiment, the resulting 4×4 transformation matrix defines the transformation from the co-ordinate space of the MRI image to the tracker co-ordinate space, thus, the transformation matrix from the tracker co-ordinate space to the co-ordinate space of the MRI image is the inverse of the determined 4×4 transformation matrix.

Figure 12:
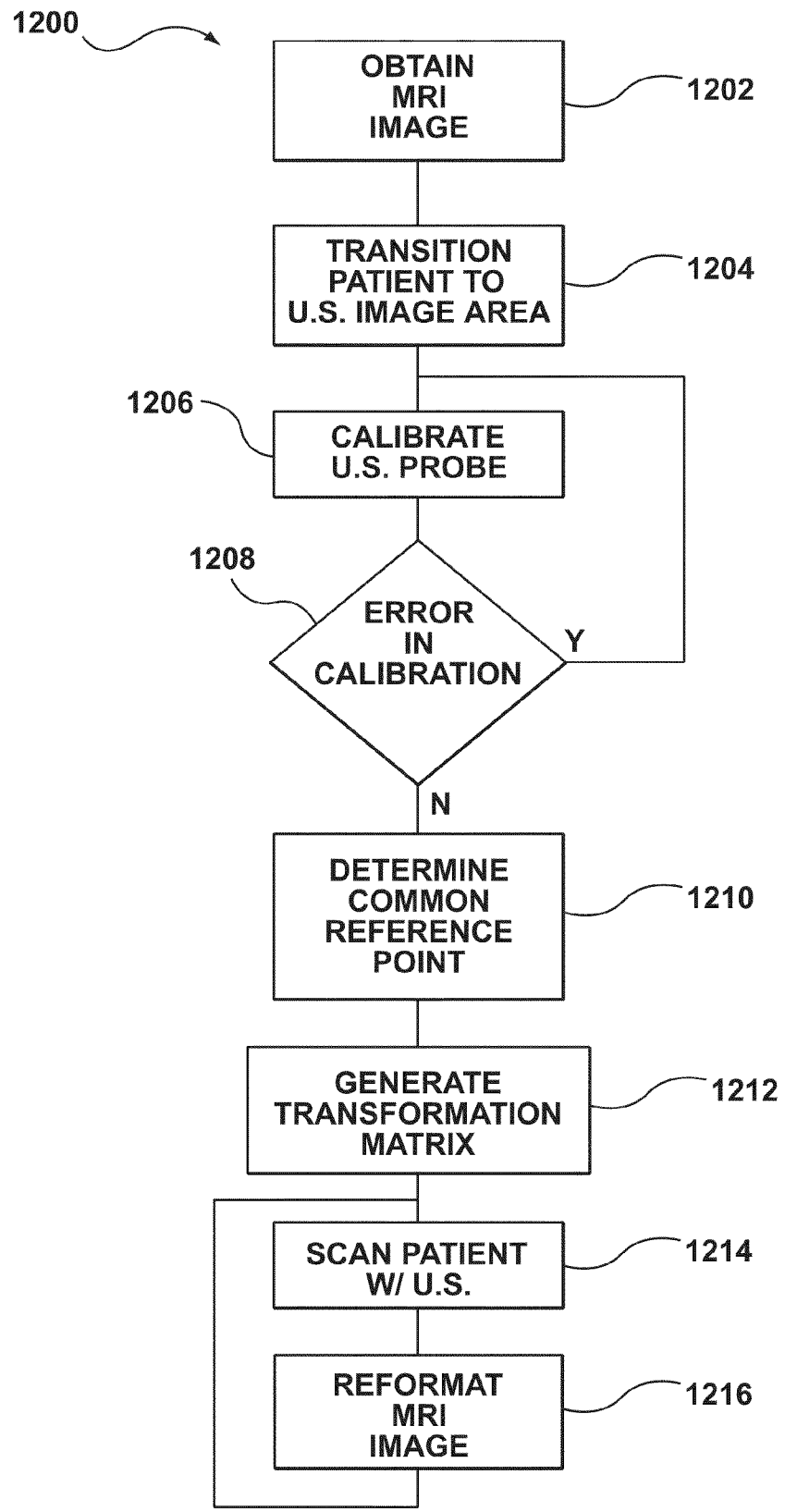
FIG. 12 shows an embodiment of a method for dynamically transforming a displayed MRI image.

Referring to FIG. 12, an embodiment of method 1200 is shown representing the use of system 100. At 1202, patient 216 is positioned in an MRI system to obtain an MRI image of a tissue of patient 216.

An MRI image of a tissue of patient 216 is obtained using MRI system 106 and is transmitted, via communication network 110 to navigation system 102. Skilled persons will understand that alternatively, the transmission of the obtained MRI image is not required to occur immediately after the MRI image is obtained, but can be transmitted upon request of navigation system 102 or can be transported by a user on a transportable media device, for example a flash drive, CD-ROM or diskette. Additionally, in some embodiments, navigation system 102 can access the MRI image remotely via communication network 110.

At 1204, patient 216 is transported to an ultrasound imaging area for ultrasound imaging by ultrasound imaging system 104. In some embodiments, the ultrasound imaging area is in the same location as MRI imaging system 106 and patient 216 does not need to be physically moved to the ultrasound imaging area, but instead, ultrasound imaging system 104 is brought to patient 216, who remains in the same position they were in during MRI imaging.

At 1206, ultrasound imaging system 104 is calibrated with navigation system 102. In some embodiments, display 810 prompts a user to position stylus 212 on corners of transducer 206 and upon positioning of stylus 212 on each of the corners of transducer 206, the user provides a user acknowledgement to navigation system 102, typically using a user interface device such as a keyboard, mouse, touch screen or foot pedal, to acknowledge that the stylus 212 is at the desired position.

The position and orientation of ultrasound probe 204 and stylus can be monitored by tracking system 108, in some embodiments ultrasound probe 204 being fitted with ultrasound transmitters 250 and stylus being fitted with stylus transmitters 252, each being monitored by optical camera 218 which transmits data to navigation system 102 representing the physical position and orientation of each of ultrasound probe 204 and stylus 212.

After the user has acknowledged each of the user prompts provided during the configuration process at 1206, at 1208 navigation system 102 error checks the calibration performed at 1206. If an error in calibration is detected, the user must recalibrate ultrasound imaging system 104 with navigation system 102.

If the calibration performed at 1206 is error free, at 1210 the transformation matrix is determined by navigation system 102, which can be used to transform co-ordinates in the co-ordinate frame of transducer 206 into co-ordinates in the MRI image.

At 1214 the user performs an ultrasound scan of the tissue of patient 216 using ultrasound imaging system 104. In some embodiments, the user administers ultrasound gel to the surface of the tissue being imaged with ultrasound probe 204 and the user positioned ultrasound probe 204 to desired positions to obtain images. In some embodiments, ultrasound system 104 displays the obtained ultrasound image on display 602.

At 1216, navigation system 102 displays and reformats the MRI image displayed on display 810 so that the slice of the MRI image shown is in the same plane and orientation that ultrasound imaging system 104 is imaging the tissue of patient 216 and is concurrently displayed by ultrasound imaging system 104. At 1216, the series of reformatted images of MRI image displayed on display 810 can be stored on navigation system 104, or in some embodiments on a data storage medium, for subsequent play back by a user on navigation system 104 at a later point in time.

The present invention has been described with regard to specific embodiments; however, it will be obvious to persons skilled in the art that a number of variants and modifications can be made without departing from the scope of the invention as described herein.

The invention claimed is:

1. A method for transforming a displayed three-dimensional image corresponding to a position and orientation of a field of view of an imaging probe, the method comprising:
    displaying a three-dimensional image of a tissue having a first co-ordinate space;
    calibrating the field of view of the imaging probe in a second co-ordinate space to a plurality of transmitters removably connected to the imaging probe, the plurality of transmitters operable to determine the position and orientation of the field of view relative to the positions of the plurality of transmitters in the second co-ordinate space,
    wherein calibrating the field of view of the imaging probe comprises:
        positioning an end of a configuration tool, the configuration tool having at least one transmitter, at a plurality of configuration positions on a transducer of the imaging probe,
        recording a location of the configuration tool at each of the plurality of configuration positions on the transducer, and
        determining a calibration matrix based on the recorded location of the configuration tool at each of the plurality of configuration positions on the transducer,
        wherein the plurality of configuration positions are corners of a face of the transducer,
        wherein a co-ordinate frame of the transducer in the second co-ordinate space has an origin (O) at a midpoint of the corners of the face of the transducer, and
        wherein the calibration matrix uses at least the origin (O) to relate the co-ordinate frame of the transducer to a co-ordinate frame of the plurality of transmitters in the second co-ordinate space;
    co-registering the first and the second co-ordinate spaces;
    transforming the position and orientation of the field of view in the second co-ordinate space to the first co-ordinate space; and
    displaying the three-dimensional image to correspond to the transformed position and orientation of the field of view.

2. The method of claim 1, wherein the calibration matrix is a 4×4 matrix and is determined by:
    determining the origin (O) specified in co-ordinates in the co-ordinate frame of the plurality of transmitters;
    determining a first vector (X) that is normal to the face of the transducer at the origin (O) specified in co-ordinates in the co-ordinate frame of the plurality of transmitters;
    determining a second vector (Y) that is perpendicular to the field of view and contains the origin (O) specified in co-ordinates in the co-ordinate frame of the plurality of transmitters;
    determining a third vector (Z) that is orthogonal to the first and second vectors and contains the origin (O) specified in co-ordinates in the co-ordinate frame of the plurality of transmitters; and
    defining the calibration matrix as [X Y Z O; 0 0 0 1] capable of relating the co-ordinate frame of the transducer to the co-ordinate frame of the plurality of transmitters in the second co-ordinate space.

3. The method of claim 2, wherein the transducer is curvilinear in shape and the method further comprises shifting the position of the origin (O) to compensate for the curvilinear shape of the face of the transducer.

4. The method of claim 1, further comprising checking for errors in calibrating the field of view.

5. The method of claim 1, wherein the co-registering of the first and second co-ordinate spaces comprises determining a 4×4 transformation matrix having a rotational component and a translational component.

6. The method of claim 5, wherein
    the rotational component is determined by:
        selecting an anatomical plane;
        determining the orientation of the selected anatomical plane in the first co-ordinate space;
        positioning the imaging probe in the orientation of the anatomical plane;
        determining the rotational component from the relative rotational differences between the orientation of the field of view of the imaging probe in the second co-ordinate space with the selected anatomical plane in the first co-ordinate space; and
    the translational component is determined by:
        selecting a landmark in the three-dimensional image, the landmark having a position in the first co-ordinate space;
        locating the landmark in the field of view;
        determining the position of the landmark in the second co-ordinate space; and
        determining the translational component from the relative difference between the position of the landmark in the first co-ordinate space and the position of the landmark in the second co-ordinate space.

7. The method of claim 6, wherein determining the position of the landmark in the second co-ordinate space comprises:
    determining an axial distance to the landmark, wherein the axial distance is the perpendicular distance from the landmark to a line formed between an upper right corner of the field of view and an upper left corner of the field of view; and
    determining a lateral distance to the landmark, wherein the lateral distance is the distance to the landmark from a midpoint of the line when the landmark is projected onto the line.

8. The method of claim 7, wherein the field of view is curvilinear in shape and the method further comprises offsetting the axial distance to compensate for the curvilinear shape of the field of view.

9. The method of claim 6, wherein the landmark is an internal tissue landmark.

10. The method of claim 6, wherein the landmark is an external landmark.

11. The method of claim 1, wherein the three dimensional image is a magnetic resonance imaging (MRI) image and the imaging probe is an ultrasound imaging probe.

12. An apparatus for transforming a displayed three-dimensional image corresponding to a position and orientation of a field of view of an imaging probe, the apparatus comprising:
    a three-dimensional image of a tissue having a first co-ordinate space;
    a tracking module in communication with a tracking system capable of tracking positions of a plurality of transmitters removably connected to the imaging probe;
    a calibration module capable of calibrating the field of view of the imaging probe relative to the tracked positions of the plurality of transmitters in a second co-ordinate space at least in part by determining a calibration matrix based on a recorded location of a configuration tool, the configuration tool having at least one transmitter, at each of a plurality of configuration positions on a transducer of the imaging probe responsive to positioning an end of the configuration tool at the plurality of configuration positions on the transducer and recording the location of the configuration tool at each of the plurality of configuration positions;

a transformation module capable of co-registering the first and the second co-ordinate spaces;

an image processing module capable of transforming the position and orientation of the field of view in the second co-ordinate space to the first co-ordinate space; and a display capable of displaying the three-dimensional image to correspond to the transformed position and orientation of the field of view, wherein the plurality of configuration positions are corners of a face of the transducer, wherein a co-ordinate frame of the transducer in the second co-ordinate space has an origin (O) at a midpoint of the corners of the face of the transducer, and wherein the calibration matrix uses at least the origin (O) to relate the co-ordinate frame of the transducer to a co-ordinate frame of the plurality of transmitters in the second co-ordinate space.

13. The apparatus of claim 12, further comprising an error correction module capable of checking for errors in calibrating the field of view.

14. A non-transitory computer-readable medium having instructions thereon for causing a processor to execute the instructions, the instructions adapted to be executed to implement a method for transforming a displayed three-dimensional image corresponding to a position and orientation of a field of view of an imaging probe, the method comprising:

displaying a three-dimensional image of a tissue having a first co-ordinate space;

calibrating the field of view of the imaging probe in a second co-ordinate space to a plurality of transmitters removably connected to the imaging probe, the plurality of transmitters operable to determine the position and orientation of the field of view relative to the positions of the plurality of transmitters in the second co-ordinate space, wherein calibrating the field of view of the imaging probe comprises:

positioning an end of a configuration tool, the configuration tool having at least one transmitter at a plurality of configuration positions on a transducer of the imaging probe, recording a location of the configuration tool at each of the plurality of configuration positions on the transducer, and determining a calibration matrix based on the recorded location of the configuration tool at each of the plurality of configuration positions on the transducer, wherein the plurality of configuration positions are corners of a face of the transducer, wherein a co-ordinate frame of the transducer in the second co-ordinate space has an origin (O) at a midpoint of the corners of the face of the transducer, and wherein the calibration matrix uses at least the origin (O) to relate the co-ordinate frame of the transducer to a co-ordinate frame of the plurality of transmitters in the second co-ordinate space;

co-registering the first and the second co-ordinate spaces;

transforming the position and orientation of the field of view in the second co-ordinate space to the first co-ordinate space; and displaying the three-dimensional image to correspond to the transformed position and orientation of the field of view.

15. A method of determining co-ordinates of a landmark visible in a field of view of an ultrasound probe in a co-ordinate space, the method comprising:

calibrating the field of view of the ultrasound probe with a plurality of transmitters removably connected to the imaging probe, the plurality of transmitters operable to determine the position and orientation of the field of view relative to the positions of the plurality of transmitters in the co-ordinate space;

determining a calibration matrix based on a recorded location of a configuration tool, the configuration tool having at least one transmitter, at each of a plurality of configuration positions on a transducer of the imaging probe responsive to positioning an end of the configuration tool at the plurality of configuration positions on the transducer and recording the location of the configuration tool at each of the plurality of configuration positions, wherein the plurality of configuration positions are corners of a face of the transducer, wherein a co-ordinate frame of the transducer has an origin (O) at a midpoint of the corners of the face of the transducer, and wherein the calibration matrix uses at least the origin (O) to relate the co-ordinate frame of the transducer to a co-ordinate frame of the plurality of transmitters in the co-ordinate space;

determining the co-ordinates of the landmark in the field of view relative to a midpoint of a line formed between the upper right corner of the field of view and an upper left corner of the field of view by:

determining an axial distance to the landmark in the field of view, wherein the axial distance is the perpendicular distance from the landmark to the line; and determining a lateral distance to the landmark in the field of view, wherein the lateral distance is the distance to the landmark when the landmark is projected onto the line; and transforming the co-ordinates of the landmark in the field of view into the co-ordinate space using the calibration matrix.

16. The method of claim 15, wherein the transducer is curvilinear in shape and the method further comprises offsetting the axial distance to compensate for the curvilinear shape of the transducer.

* * * * *